(12) United States Patent
Selvaganapathy et al.

(10) Patent No.: US 8,702,939 B2
(45) Date of Patent: Apr. 22, 2014

(54) ELECTROTAXIS METHODS AND DEVICES

(75) Inventors: Ravi (Ponnambalam) Selvaganapathy, Hamilton (CA); Bhagwati Gupta, Dundas (CA); Pouya Rezai, Dundas (CA)

(73) Assignee: McMaster University, Hamilton (CA)

( * ) Notice: Subject to any disclaimer, the term of this patent is extended or adjusted under 35 U.S.C. 154(b) by 53 days.

(21) Appl. No.: 13/234,039

(22) Filed: Sep. 15, 2011

(65) Prior Publication Data

US 2012/0061240 A1    Mar. 15, 2012

Related U.S. Application Data

(60) Provisional application No. 61/383,011, filed on Sep. 15, 2010.

(51) Int. Cl.
*G01N 27/447* (2006.01)
*B03C 9/00* (2006.01)

(52) U.S. Cl.
USPC ............... 204/450; 435/173.9; 435/287.1; 435/288.7; 435/7.1; 422/82.01; 382/128; 382/133; 119/840

(58) Field of Classification Search
USPC ............. 204/450, 451, 600, 601, 604, 549; 435/7.1, 6.1, 288.7, 173.9, 287.1; 119/840; 382/126, 133; 422/68.1, 422/82.01

See application file for complete search history.

(56) References Cited

U.S. PATENT DOCUMENTS

2006/0254920 A1*  11/2006  Gascoyne et al. ............ 204/547

OTHER PUBLICATIONS

Sukul et al. (Journal of Nematology, vol. 10, No. 4, 1978, 314-317).*
Gabel et al. (Journal of Neuroscience, Jul. 11, 2007, 27(28), 7586-7596).*
Huang et al. (Biosensors and Bioelectronics 24, May 19, 2009,3510-3516).*
Rezai et al. (Lab Chip, Nov. 13, 2009, 10, 220-226).*
Khew et al. (Phytopathology 64:500-507, Oct. 25, 1973).*

* cited by examiner

*Primary Examiner* — Jennifer Dieterle

(57) ABSTRACT

A method of controlling nematode response in a microfluidic environment is provided comprising exposing the nematode to an electric field that induces a nematode response. In one embodiment, a method of sorting a group of nematodes based on a selected parameter is provided comprising the step of exposing the nematodes to an electric field that induces a differential response among the nematodes based on the selected parameter, wherein the differential response functions to separate the nematodes based on the selected parameter. Devices useful to achieve these methods are also provided.

10 Claims, 28 Drawing Sheets

ELECTROTAXIS METHODS AND DEVICES

This application claims the benefit of U.S. Provisional Application No. 61/383,011, filed on Sep. 15, 2010, and incorporates such provisional application in its entirety by reference.

FIELD OF THE INVENTION

The invention generally relates to methods which utilize electrotaxis, and in particular, relates to methods of controlling the movement of nematodes in a microfluidic environment, and devices useful to conduct such methods.

BACKGROUND OF THE INVENTION

The objective of the majority of biological research today is to understand human diseases and develop new and effective treatments for them. Multidisciplinary research approaches serve to identify the genetic basis of disease in order to better understand and treat them. Due to the enormous complexity of cellular and molecular processes, as well as ethical issues associated with experiments on human subjects, researchers have focused on a number of eukaryotic systems that are simpler and easier to manipulate, yet complex enough to address many of the questions relevant to human biology. For instance, neurodegenerative diseases result from the progressive loss of neurons in the brain. The hallmark of these diseases is the accumulation of certain proteins inside the neuronal cells, leading to the loss of function, structure and, ultimately death of the cell. Finding treatments or cures for these diseases is challenging as very little is known about the underlying causes of these diseases.

Animal models offer an ideal system to observe the implications of complex interaction of the disease mechanism in the whole organism. The nematode, *Caenorhabditis elegans* (*C. elegans*), is one such model organism that has greatly facilitated the study of conserved biological processes. It offers a number of useful features such as small size (~1,000 somatic cells), well-mapped neuronal connectivity, transparency, short life cycle (~2.5 days), and the ability to generate many progeny in a relatively short time. Furthermore, the identity and lineage of every cell in the worm is known which enables researchers to address biological questions at single cell resolution. The amenability of the organism to genetic analysis has led to isolation of a large pool of mutant strains that can be effectively used to study gene function in regulating various developmental, behavioural, and physiological processes. Such studies have established the roles of many genes (e.g. HOX family members) and signalling pathways (e.g. Ras) in normal and disease processes, thereby facilitating the study of their homologues in other organisms including humans.

The analysis of the *C. elegans* genome sequence has revealed the presence of a large number (~65%) of human disease orthologs that are very useful in investigating the underlying mechanism of gene function. Worms have been used successfully as models for a variety of human disorders such as obesity, hypertension, Duchenne's Muscular Dystrophy (DMD), and neurodegeneration (e.g., Huntington's disease, HD; Parkinson's disease, PD). Researchers have established mutant strains for these diseases that serve as models to study the underlying mechanism as well as to search for chemical compounds/drugs to inhibit the defects. For example, in the case of the *C. elegans* HD model, chemical screening has identified two compounds, mithramycin (MTR) and trichostatin A (TSA), that have significant effect on promoting neuronal survival. PD also results from the loss of dopamine neurons. PD patients show motor symptoms such as slow, imbalance body movement, stiffness of body (akinesia). Current treatments (such as levodopa, bromocriptine, cabergoline, lisuride and pergolide) provide only a temporary relief but cannot cure patients completely. This is because of the poor understanding of the etiology of PD. *C. elegans* PD models have been generated that show degeneration of DA neurons and movement defects. *C. elegans* has almost all the genes involved in Parkinson's disease, making it possible to study the genetic basis of the disease. Importantly, the mechanism for dopamine transportation and signalling are conserved between human and *C. elegans*. *C. elegans* has a simple dopamine neuron system consisting of only eight neurons; two pairs of CEPs, a pair of ADE in the head region and another pair of PDE in the mid body.

In addition to mutations in PD-associated genes, exposure of certain chemicals, such as 6-hydroxy dopamine (6-OHDA), methyl phenyl tetrahydro pyridine (MPTP) and rotenone (a pesticide), also induces PD-like symptoms in humans and other animal models, including *C. elegans*. These neurotoxins work, in part, by causing degeneration of DA neurons. 6-OHDA is also endogenously produced by the dopamine neurons as a byproduct of dopamine and inhibits the mitochondrial respiratory enzyme complex I and IV. MPP+ is the active toxic product of MPTP that inactivates the mitochondrial enzyme complex I of respiratory chain. Toxin exposed worms have been shown to serve as effective PD models to study the basis of neurodegeneration. These models also facilitate screening of genes and compounds that protect neurons from toxin-induced damage.

Among the various features of *C. elegans*, its small size and the ability to grow in liquid media have facilitated high throughput screenings (HTS) for chemicals. Chemicals which affect physiological processes, thus, may serve as potential drug candidates for a variety of medical applications. Conventional methods of chemical and animal screening involve exposure of a certain population of synchronized-age or -mutant model animals to thousands of chemical compounds individually and inside multi-well plate dishes, while monitoring the subsequent effects of the drugs on animals' growth, fertility, and other biological processes by immobilization and visual inspection. The above-mentioned methods are either manual and hence prone to human errors and time-consuming, or robotically automated and hence expensive and inaccessible to the majority of researchers. In addition, most conventional plate-based methods are currently focused on the cellular level analysis and tend to ignore the movement behaviour of *C. elegans* as one the most important parameters (especially for movement disorder diseases). Cellular level analysis is mostly done through immobilization and GFP imaging. Methods for immobilizing worms (anesthesia or gluing) are fatal, non-reversible and not suited for post-experimentation studies. The glue or anaesthetic chemical compositions' effect on *C. elegans* biological processes is also not well understood.

Microsystem engineering has played a critical role in providing the necessary technologies to tackle the challenges of small organisms' manipulation and analysis. *C. elegans* worms survive in liquid environment and due to their matching size scale with microfluidics (submicron to hundreds of micrometers), they have recently been studied in such devices. This has resulted in a dramatic increase in the experimental accuracy, consistency (by removing human interferences) and decrease in the cost of automation. Recently, microfluidic devices have been used for more precise and quantitative analysis of *C. elegans* development and behaviour. These devices have also been used for analyzing nematodes behaviour and mechanical characteristics in response to diverse stimuli, in-vivo imaging of their neuronal activity, culturing, sorting and screening, and in-vivo studies of neuronal regeneration after laser nano and micro-surgery on individual animals. These microfluidic devices have significantly facilitated assays on worms in an automated high throughput manner. In order to visualize and manipulate animals within these environments, their natural movement is eliminated by the use of hydraulic and pneumatic flows and forces. Accordingly, these devices are complicated in terms of fabrication (multilayers of PDMS microstructures aligned and bonded together) and operation (computer-controlled pneumatics). Also, despite being advantageous in phenotypic, cellular and sub-cellular studies, these devices are not suitable for performing movement-related behavioural studies on worms.

SUMMARY OF THE INVENTION

Novel methods and devices have now been developed that are useful to control the movement of nematodes in an electric field.

Thus, in one aspect, a method of a response in a nematode in a microfluidic environment is provided comprising exposing the nematode to an electric field that induces the selected nematode response.

In another aspect, a method of sorting nematodes based on a selected parameter is provided comprising the step of exposing nematodes to an electric field that induces a differential response among the nematodes based on the selected parameter, wherein the differential response functions to separate the nematodes based on the selected parameter.

In another aspect, a microfluidic sorting device useful to sort nematodes is provided comprising:
- a nematode reservoir that feeds into a separation channel having a proximal end and a distal end;
- a series of collection channels that extend perpendicularly from the separation channel along the length of the separation channel, wherein each collection channels houses a collection electrode;
- an accumulation electrode adjacent to the reservoir at the proximal end of the separation channel; and
- a separation electrode at the distal end of the separation channel.

In another aspect, a field flow fractionation device is provided comprising at least one separation channel having an inlet at its proximal end and a plurality of collection channels at its distal end, wherein the separation channel comprises a plurality of micropillars spaced throughout the separation channel which function to maintain non-responsive nematodes moving towards the collection channels, and separation electrodes positioned along each side of the separation channel to provide an electric field within the separation channel perpendicular to a flow from the inlet to the collection channels.

A continuous flow sorter device is provided in a further aspect comprising:
- multiple parallel microchannels, each of said microchannels comprising an inlet at a proximal end and a collection chamber at a distal end thereof, wherein each of said microchannels is separated by an array of linearly spaced micropillars, wherein the micropillars are equidistantly spaced between each microchannel and wherein the spacing between micropillars decreases from the first microchannel and for each subsequent microchannel; and
- an electrode adjacent to the first and last microchannels of the multiple microchannels for the application of an electric field across the width of the device.

A nematode storage microchamber device is provided in another aspect. The device comprises a central chamber comprising an inlet channel through which worms can be loaded into the device and an outlet channel for removal of the worms; and an entropic trap comprising an electrode connecting each of said inlet and outlet channels to the central chamber, wherein said entropic trap prevents the movement of worms therethrough except on application of an electric field across the trap.

In a further aspect, a microfluidic channel array is provided comprising: an array of parallel microchannels; a worm storage unit at a proximal end of each microchannel; an electrode-based worm detection unit at the proximal and distal ends of each microchannel; and an injection channel and fluid circulating means connected to each microchannel.

In another aspect, a method of screening candidate compounds that affect nematodes is provided comprising:
i) measuring the movement characteristics of one or more nematodes;
ii) exposing the nematodes to a candidate compound; and
iii) measuring the movement characteristics of the nematode following exposure to the compound, wherein a change in the movement characteristics of the nematode is indicative that the compound affects the nematode.

These and other aspects of the invention are described in the detailed description by reference to the following drawings.

DETAILED DESCRIPTION OF THE INVENTION

Figure 1:
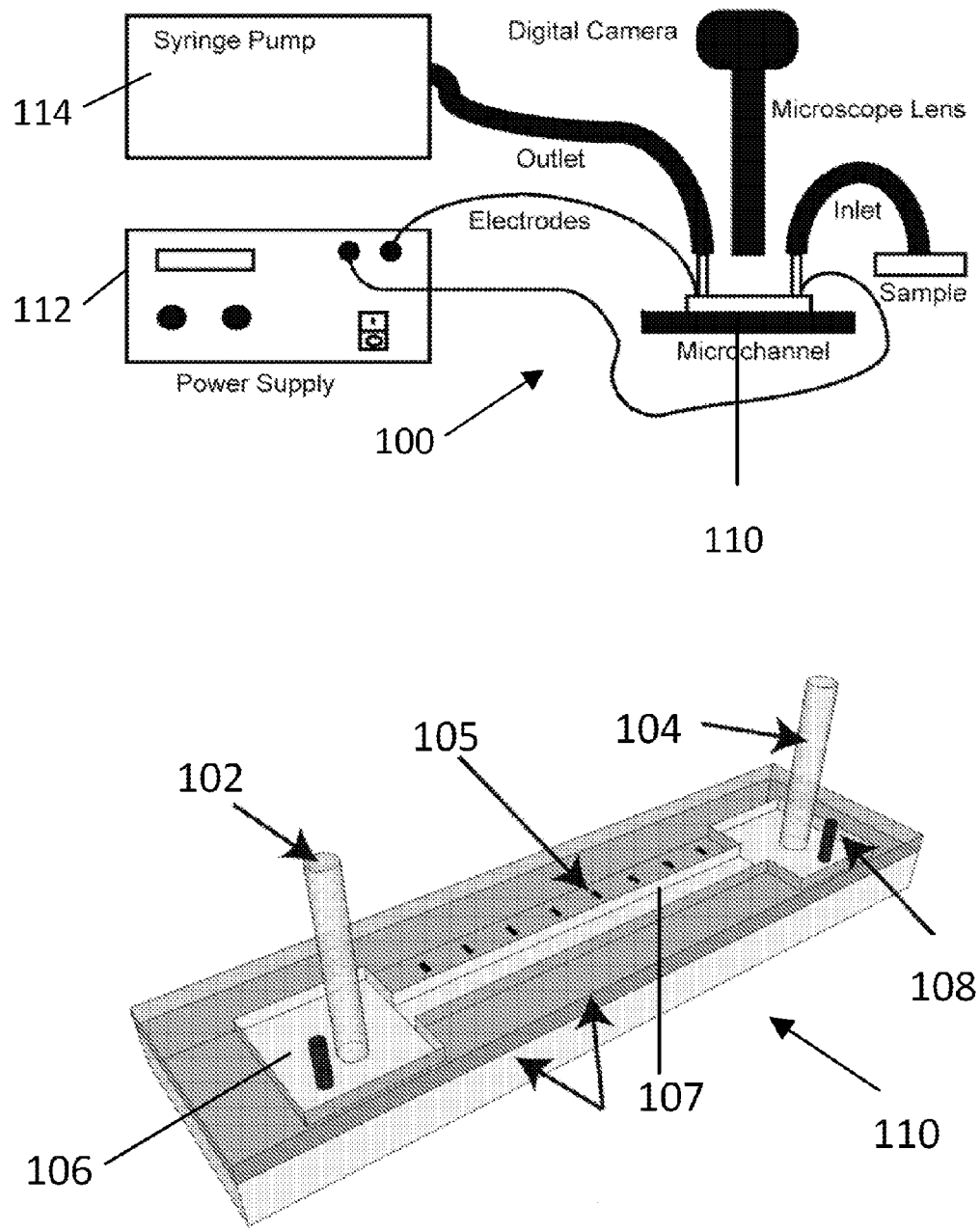
FIG. 1 illustrates a DC electrotaxis device (a) and a microchannel of the device (b)

A method of inducing a response in a nematode in a microfluidic environment is provided comprising exposing the nematode to an electric field that induces the selected nematode response. The response induced by an electric field, such as a movement-induced response i.e. electrotaxis, has been determined to be reliable and highly reproducible. The electric field can be used as a powerful stimulus to efficiently control and orient nematodes as desired. In addition, exposure to the electric field is not harmful to nematodes since they continue to live normally and remain fertile following exposure to an electric field.

The term "nematode" is used herein to refers to organisms of the animal phylum "Nematoda", e.g. round worms, and particularly, to any round worm with amphid neurons that is expected to generate a response on exposure to an electric field. Examples of nematodes include, but are not limited to, *Caenorhabditis elegans, C. briggsae* and *Oesophagotomum dentatum*.

An electrotaxis device may be used to practice the method of inducing a response in a nematode. The device uses an electrical signal to manipulate nematode movement. The device comprises a microchannel having first and second reservoirs formed at first and second ends of the microchannel. The first reservoir includes an inlet for input of a sample into the microchannel and the second reservoir includes an outlet for removal of fluid and/or sample. Each reservoir includes an electrode for use to establish an electric field between the reservoirs on connection to a power supply selected based on the electric field to be supplied (e.g. direct current vs. alternating current). As one of skill in the art will appreciate, any suitable electrode may be used such as metal electrodes, e.g. gold, copper or platinum wires, gel electrodes and liquid microchannel electrodes. Flow of sample into the microchannel via the inlet may be achieved by a suction pump connected to the outlet. The microchannel may be made of any suitable material that does not affect the application of an electric field, including polymeric materials such as organosilicon compounds. The use of Polydimethylsiloxane (PDMS) is preferred to provide a controlled environment in which the electric field is uniformly axial along the entire channel.

The present electrotaxis method may be used to sort nematodes based on a differential response between different nematodes to a given electric field. The differential response between nematodes results from a distinguishing characteristic or parameter that exists between nematodes. The parameter may be, for example, developmental stage (age), size (length), a mutation affecting function of a neuronal or muscle gene and exposure to a chemical compound or drug that affects movement. Thus, nematodes of different ages may respond differently to a given electric field. Generally, adult nematodes exhibit a greater response on exposure to an electric field when compared to non-adult nematodes (e.g. L3-L4 stage nematodes), and shorter nematodes exhibit a greater response when compared with the response of longer nematodes. The term "response" is used herein to refer to one or more movement characteristics such as direction of travel, speed of travel, paralysis, body bends, turning time, extent of head movement and sinusoidal motion path, pauses and reversals.

Thus, a method of separating nematodes based on a selected parameter is provided comprising exposing nematodes to an electric field that induces a differential response among the nematodes based on the selected parameter, wherein the differential response functions to separate the nematodes. The differential response is induced by an electric field which is selected to promote a differential response based on a given parameter. If the nematodes are to be separated based on developmental stage, then an electric field of 2 V/cm or less may be selected, which is an electric field to which early stage nematodes do not respond and to which later stage nematodes do respond. If nematodes are to be separated based on length, an electric field of greater than 4 V/cm may be selected as nematodes shorter than wildtype exhibit a stronger response when exposed to this electric field than nematodes which are longer than wildtype.

The electric field may be applied as a direct current (DC), alternating current (AC), a pulsed DC current and any other variations thereof useful for sorting purposes. The application of AC is effective to localize nematodes, holding them in position by a non-physical means, for collection or until movement by application of DC is desired. The application of pulsed DC is effective to induce a turning response in nematodes.

Various methods and microfluidic devices useful to achieve sorting by electrotaxis are also provided.

In one embodiment, a method of sorting is provided comprising the steps of accumulating nematodes at the proximal end of a separation channel on application of an accumulating electric field, inducing the nematodes to move along a separation channel by application of a separating electric field, and collection of separated nematodes in separate collection channels by application of a collecting electric field in a direction perpendicular to the separating electric field. The strength of each of the accumulating electric field, separating electric field and collecting electric field will be based on the strength of field suitable to achieve the desired action. Thus, the strength of the accumulating electric field may be in the range of about 2-16 V/cm, and the strength of the collecting electric field may be in the range of about 2-16 V/cm. The strength of the separating electric field will depend on the characteristics of the organisms to be separated, as discussed above, and in more detail herein.

A microfluidic sorting device useful to conduct the sorting method is provided. The sorting device comprises a nematode reservoir that feeds into a separation channel. A series of collection channels extend perpendicularly from the separation channel along the length of the separation channel. An accumulation electrode is positioned adjacent to the reservoir at the proximal end of the separation channel, a separation electrode is positioned at the distal end of the separation channel and a collection electrode is positioned within each collection channel. A cathodic potential is applied to the accumulation electrode to accumulate the nematodes. Following accumulation of the nematodes, a cathodic potential is then applied to the separation electrode to induce movement of the nematodes along the separation channel towards the separation electrode. Following sufficient separation of the nematodes within the separation channel, a cathodic potential is applied to the collection electrodes to generate an electric field that is perpendicular to the separation channel (in the direction of the collection channels) to move separated nematodes into separate collection channels.

A continuous field flow fractionation-type separation method is also provided. In this method, electric field is applied in a direction perpendicular to the direction of nematode movement in a pressure driven flow. Depending on the strength of electric field applied and the electrotactic response of the nematodes, they are fractionated into sub-groups continuously. Thus, the method comprises the steps of flowing nematodes through a separation channel in a first direction, applying an electric field to the separation channel in a direction perpendicular to the first direction to cause separation of the nematodes based on their response to the electric field and collecting the separated nematodes. As one of skill in the art will appreciate, the strength of the electric field is selected to achieve separation of a target nematode population from a mixture of nematodes.

A continuous field flow fractionation device suitable to conduct continuous field flow fractionation is provided which comprises a separation channel having an inlet at its proximal end and a plurality of collection channels at its distal end. Separation electrodes are positioned along each side of the separation channel to provide an electric field on actuation of a power supply across the separation channel and perpendicular to nematode flow from the inlet to the collection channels. The separation channel may comprise a plurality of micropillars which function to maintain non-responsive nematodes (e.g. nematodes that do not exhibit electrotaxis) moving in a straight line towards the collection channels to facilitate separation. The micropillars may be equidistantly spaced in straight lines throughout the separation channel. Thus, nematodes are input into the device at the inlet by a pressurized flow towards the proximal collection channels. An electric field applied perpendicular to this flow between separation electrodes causes separation of the moving nematodes based on their response to the selected electric field, followed by collection of the separated nematodes in the collection channels.

In a further embodiment, an electric trap device is provided comprising a microchannel having a reservoir formed at first and second ends thereof which are connected by a channel comprising a narrowed electric trap portion. Each reservoir includes an electrode for connection to a DC power supply to generate an electric field across the microchannel from one reservoir to the other reservoir. The strength of the electric field is increased within the electric trap portion from the field applied to the microchannel. A first reservoir includes an inlet for input of nematodes, while the second reservoir includes an outlet for removal of fluids/sample. In use, nematodes are delivered into the first reservoir via the inlet and a constant electric field is applied between electrodes to induce electrotaxis of the nematodes towards the narrow electric trap. As the narrowed electric trap has an increased electric field, it functions to separate nematodes based on their ability to withstand the increased electric field, e.g. are not paralyzed by the increase in electric field strength. Nematodes that can withstand the increase in the electric field within the electric trap (and are not paralyzed by it), will pass through the trap to the second reservoir; however, if the electric field within the trap is such that it will paralyze the nematode (this is discernable by the nematode), the nematode will not pass through the trap.

Thus, a method of separation which utilizes electric trapping is provided. The method comprises the steps of inducing nematodes by application of a first electric field to move through a channel towards a narrow trap portion of the channel which exhibits a second electric field of greater strength than the first electric field such that it either permits or prevents passage of a target population of nematodes through the trap portion. The narrow trap portion of the channel exhibits a second electric field of increased strength such that certain populations of nematodes will not pass through the trap because the increased electric field within the trap is paralysis-causing.

A continuous flow sorter device is also provided. The device comprises multiple parallel microchannels with an array of spaced micropillars between each microchannel. The micropillars are equidistantly spaced between each microchannel, with decreasing spacing between micropillars from the first microchannel to each subsequent microchannel (e.g. spacing between micropillars decreases from the spacing of micropillars at the first microchannel to the spacing between micropillars of each subsequent microchannel, e.g. micropillar gaps between the first set of micropillars=100 um, micropillar gaps between the second set of micropillars=70 um, and micropillar gaps between the third set of micropillars=40 µm), thereby forming electric trap arrays of decreasing width which exhibit increasing electric field strength as width decreases. Inlets are provided at the proximal end of each microchannel through which a flow of liquid/sample may be input via a pump into the device, and a series of collection chambers exist at the distal end of each microchannel to collect sorted worms. Electrodes are situated along the length of the device adjacent to the first and last microchannels of the multiple microchannels for the application of an electric field across the width of the device.

A method of sorting using the continuous flow sorter comprises input of nematodes at the inlet of the first microchannel at a continuous flow rate, application of an electric field in a direction perpendicular to nematode flow sufficient to induce electrotaxis in select target nematodes. The select nematodes are then subjected to electric traps of increasing electric field strength such that separation of nematodes occurs when the field strength of an electric trap allows passage of some nematodes and prevents passage of other nematodes.

A semi-continuous sorting device is also provided. The device comprises a plurality of parallel electric traps which connect a loading chamber or reservoir to a separation chamber or reservoir. Electrodes situated at each of the loading and separation chambers provide a constant electric field from the loading to the separation chambers along the length of the electric traps on actuation (e.g. connection to a power source). Sorting of nematodes using this sorting device is similar to sorting achieved in a device with a single electric trap. Sorting is achieved by selection of an electric field that induces select nematodes to move from the loading chamber through the increased electric field within the electric traps to the separation chamber, while other nematodes are prevented from passing through the electric traps due to the increase field strength that occurs therein.

A worm storage microchamber device is provided in another aspect of the invention. The storage device comprises a central chamber (e.g. 1-20 mm), which may be of any shape, for example, ring-shaped or an irregular ring-like shape, and includes a microfluidic inlet channel through which worms can be loaded into the device, and a microfluidic outlet channel for removal of the worms from the device. A narrow entropic trap (e.g. a width of about 10-200 um) comprising an electrode connects the inlet and outlet channels to the central chamber and prevents the movement of worms from the chamber into the channels. Worms inherently prefer to move without confinement. The entropic trap is of a size that restricts worm flexibility of movement. This reduction in entropy of movement leads to the worm to remain in the chamber. However, application of an electric field across the trap leads to a motive force that overrides the confinement effects, allowing the worm to progress through the trap at the inlet or outlet.

A microfluidic channel array is also provided in a further aspect in order to analyse the movement of multiple single worms at one time. Worms can be arrayed into individual microchannels and their movement analysed on exposure to a drug or other chemical compound. Entropic traps at the mouth of each microchannel along with application of an electric field serve as a valve to allow movement of worms into individual microchannels. A electrical impedance sensor at the mouth of the microchannels near the trap will sense the arrival of the worm and cut off the trap electric field preventing any further worms from entering the microchannel. This feedback mechanism allow automatic arraying of several microchannels in parallel and ensure that each microchannel has a single worm. These microchannels also integrate electrical or optical sensors that can initiate electrotaxis and measure the speed of the worm. Regions in which drugs of various types and concentrations can be dosed to determine their effect on the electrotactic speed of the worm are incorporated as described in detail herein.

The present electrotaxis method may be used in movement-based high-throughput screening methods to identify candidate compounds that affect movement in selected nematode populations that may, for example, be representative of disease. Thus, a method of screening candidate compounds that affect nematode movement is provided comprising measuring the initial or control movement characteristics of one or more nematodes, and then following exposure of the nematodes to a candidate compound, measuring the compound-induced movement characteristics of the nematode. A change in the movement characteristics of the nematode is indicative that the compound affects the nematode, e.g. to improve movement characteristics or to hamper movement characteristics.

For example, a combination of null mutations in dystrophin (dys-1) and MyoD (hlh-1) genes in *C. elegans* has been shown to cause progressive muscle degeneration similar to human DMD (Duchenne's Muscular Dystrophy) that impairs movement. The present electric field-based microfluidic channels may be used to screen for compounds that improve/restore movement in this mutants, thereby identifying potential candidates to test in human DMD patients. Additionally, electric field-based assays may be used to study the mechanism of electrotaxis, as well as how the nervous system processes extracellular signals. Because movement is a complex behaviour that is controlled by many genes, the present methods will be useful to study the function of genes and pathways that mediate this behaviour.

In another example, the present methods may be used to study neurodegeneration in *C. elegans*. Though the molecular mechanism of electrotaxis is yet to be elucidated, it is known to be mediated by neurons, most of which are located in the head region (e.g. amphid sensory neurons). Thus, an electrotaxis method of screening for compounds having neuroprotective properties in certain nematode populations (mutants). In this regard, the effect of a known neuroprotective compound, acetaminophen, was determined to be neuroprotective to nematodes exposed to neuro-toxic compounds such as 6-OHDA, MPTP and Rotenone.-induced. These results demonstrate that the present microfluidics electrotaxis-based assay system is a powerful and sensitive way to study neurodegeneration and identify neuroprotective chemicals in *C. elegans*.

Embodiments of the invention are described by reference to the following detailed examples which are not to be construed as limiting.

EXAMPLE 1

Electrotaxis Device

An electrotaxis device suitable to study nematode response to an electric field is provided, as shown in FIG. 1*a*. The device 100 comprises a microchannel 110, as shown in FIG. 1*b*, having a reservoir 106 formed at both ends thereof. The reservoirs 106 are connected via an assay channel 107 along the edge of which is an optional length scale 105. One reservoir includes an inlet 102 for input of a sample into the microchannel, and the other reservoir includes an outlet 104 for the removal of fluid and/or sample. Each reservoir 106 also includes an electrode 108 to establish an electric field from one reservoir to the other reservoir by connection to a power supply 112. Flow of sample into the microchannel 110 via inlet 102 may be achieved by a suction pump 114 connected to outlet 104.

In one embodiment, the device may comprise: (i) a worm handling unit (syringe pump, sample container, inlet, and outlet pipes), (ii) a monitoring unit (digital camera and microscope lenses), (iii) an actuation unit (power source and electrodes), and (iv) a microchannel device (sealed PDMS microchannel with embedded electrodes in reservoir areas). The microdevice consists of a simple microchannel instrumented with electrodes (5 cm apart) within the reservoirs.

The microchannel 110 of the device 100 may be any appropriate size, including, e.g. 300 µm-wide, 80 µm-deep, and 5 cm-long. In one embodiment, the microchannel 110 was fabricated using soft lithography as described (Xia et al. Annu. Rev. Mater. Sci., 1998. 28: p. 153-184). The mask layout was designed in AutoCAD (Autodesk Inc., San Francisco, USA) and printed using ultra high-resolution laser photo plotting on transparency sheet. SU8-100 (80 µm-thick) negative photoresist (MicroChem. Corp., MA, USA) was used to lithographically pattern a master mold of the device. Polydimethylsiloxane (PDMS) pre-polymer mixture (Sylgard 184 kit, Dow Corning Corp., MI, USA; 10:1 ratio of the base and cross-linker) was then cast on the master mold, and cured at room temperature for 24 hours. The PDMS replica was then peeled off the master mold and cut into pieces containing individual channels. The inlet and outlet access ports were punched out at the reservoir areas. The top surface of the PDMS replica and a bare PDMS piece of the same size were plasma oxidized (50 W for 30 s), micro-contact printed with PDMS pre-polymer, and bonded, sealing the microchannel. Inlet and outlet capillary glass tube tips (VWR International, USA, catalog number CA14672-380, 1.5 mm outer diameter, 20 mm long) were connected to the punched areas. Plastic tubes (Saint-Gobain Performance Plastics, OH, USA, TYGON R-3603, 2.4 mm outer diameter and 10 cm long) were connected to the inlet and outlet glass tubes. Metal electrodes (Arcor Electronics, USA, C24, copper 0.5 mm diameter) were inserted into the reservoir areas by punching through the PDMS elastomer from the side. Liquid PDMS pre-polymer was then used to seal the surrounding areas of the electrodes and the device was placed on a hot plate (120° C.) to cure. The device was then attached to a glass cover slip again using PDMS pre-polymer and cured.

The inlet tube of the microchannel was placed in a petri dish containing worms and a syringe pump (KD Scientific 14-831) connected to the outlet was turned on (flow-rate=200 µl/min) to aspirate worms (one at a time) into the channel. As soon as a worm reached the middle of the microchannel, the syringe pump was turned off and the outlet pipe was disconnected from it. The inlet and outlet pipes were then leveled to the same height preventing the possibility of pressure-induced flow. The electric field (generated using KEITHLEY 2410 as a power source) was then applied and the response of the worm was recorded. Electrical resistance of the channel filled with the buffer M9 solution in all tests was ~0.68 MΩ. The videos were recorded to obtain raw data.

Nematode Strains and Culturing

Worms were grown at room temperature (20° C.) on standard NG agar plates seeded with OP50 *E. coli* bacteria as previously described by Brenner (Genetics, 1974. 77(1): p. 71-94).

The strains used in this study are: wildtype N2, BC347 unc-54(s74), CB78 unc-6(e78), PS55 lon-2(e678), and PS250 dpy-5(e61). The PS55 strain also carries a him-5 (e1490) mutation that increases frequency of males in the progeny. The N2 strain was used as a wild-type reference in all assays. All strains are available at *Caenorhabditis* Genetics Center (Minnesota, USA).

Nearly all experiments were done with synchronized stages of animals. Gravid hermaphrodites were washed off culture plates using M9 buffer (3 g KH2PO4, 6 g Na2HPO4, 5 g NaCl, and 1 ml 1M MgSO4 in 1 liter). They were centrifuged and washed twice with M9 to remove excess bacteria and debris. A 2 ml of bleach solution (800 µL of 4 N NaOH and 1,200 µL of commercial bleach) was added to 4 ml of worms. The mixture was incubated at room temperature for 3 minutes and then centrifuged and washed with M9 (at least 3×). The eggs were allowed to hatch in M9 for 24 hrs. They were subsequently transferred to NG agar plates seeded with OP50 bacteria and were allowed to grow further. When required for testing, the worms were washed again with M9 and loaded into microchannels.

For electrokinetic flow tests dead animals were obtained as below. Wild type *C. elegans* were synchronized using the above bleach protocol and kept in M9. The animals were left in the absence of food for one week at room temperature causing them to die. The dead animals appeared rod-shaped with no visible body bending or movement.

Data Analysis

A length measurement scale was microfabricated alongside the microchannel as shown in FIG. 1b. The response of worms to different ranges of electric fields was recorded by a camera (Nikon Coolpix P5100, NY, USA) and analyzed by ImageJ software (http://rsbweb.nih.gov/ij/) and AutoCAD (http://www.autodesk.com). The ImageJ software was used to analyze videos and obtain the snapshots (every 0.07 s) of recorded movies of worm movements. The sequenced images were used to measure the distance traveled by the worm inside the channel. For this purpose, the initial and final snapshots were imported into the AutoCAD software and the traveled length was measured by superimposing lines on the worms' pathway and comparing the line lengths to a reference length bar in the image. Snapshots obtained from ImageJ software was used to measure the worm movement distance between length scales fabricated on the device. The worms' lengths were also measured by linear approximation method using AutoCAD software. One image of each tested worm was imported to the software. A total of 15 lines were drawn on the worms' body image. The lengths of the lines were added and the total length was compared to the reference value to determine each worm's length. This process was repeated three times for each worm and an accuracy of about 10 µm was obtained.

Results and Discussion

An electrotaxis device incorporating a microchannel format, as shown if FIG. 1, allows electric streamlines to be confined and directed along the axis of the channel and provides a simple well-controlled format to study and understand the electrotaxis of *C. elegans*. Straight microchannels (e.g. 5 cm long and 80 µM deep) with varying widths of 2 mm, 1 mm, 500 µm, 300 µm, and 150 µm were utilized.

Synchronized *C. elegans* of various age and size, from L1 (~250 µm-long) to young adult (~1 mm-long), were loaded individually into the microchannels filled with M9 buffer and positioned in the central section (2.5 cm away from each electrode) using a syringe pump. In the absence of a stimulus, the animals had random movement in the microchannel (n=20). In some instances, it was observed that after travelling a certain distance in one direction, the animals turned and moved in the opposite direction. In two cases the animals exited the channel after spending 5 minutes inside the channel. The device having a 300 µm-wide microchannel appeared to guide movement along the channel axis without any obvious physical confinement and eliminated any perpendicular motion of the worms. The 150 µm-wide microchannel appeared to interfere with normal swimming behaviour of the worms.

In the presence of low-voltage electric fields, worms exhibited electrotaxis and moved in a directed manner towards the negative pole. To rule out the influence of electrokinetic flows (electrophoresis as well as electro-osmosis), dead worms were loaded individually into the channels filled with M9 solution and positioned in the middle section (2.5 cm away from the electrodes) using a syringe pump. A wide range of electric field strengths (1-20 V/cm) was applied across the channel that showed that electrokinetic flow above 13 V/cm was able to move dead worms towards the anode. No change in the morphology of dead worms was observed during this process. Furthermore, electrokinetic effects (electrophoresis of the worm and electro-osmosis of fluid) had no significant role in the movement of worms below 13 V/cm in these confined geometries.

To characterize the electrotactic behaviour in more detail, synchronized animals of different stages (from L1 to young adult) were introduced into the microchannel. A wide range of electric fields (1-12 V/cm) was applied across the channel and movement of animals was monitored. Early stage animals (L1 and L2) displayed no obvious response to the feasible electric field (1-12 V/cm) since they continued to swim randomly regardless of the direction and presence of the field. At later stages (L3 onwards), animals responded robustly to the electric field within a certain range that was different for each stage and exhibited directed movement towards the negative pole. A careful examination revealed that their swimming pattern was typical of unexposed animals in a liquid environment except that the response was directional. This suggests that the electric field does not distort body bends, but rather induces swimming behaviour. Below the minimum threshold, the movement was found to be random whereas above the maximum threshold, worms appeared paralyzed although they resumed swimming upon the removal of the electric field indicating that the effect was reversible. Using a length scale, fabricated alongside the microchannel, the speed under an effective electric field range of response was measured. The finding that only older worms responded to the electric field suggests that this behaviour is developmentally regulated and is likely to be mediated by certain differentiated cell types that may be absent (or immature) at earlier L1 and L2 stages. It is also possible that early stage animals respond to electric fields above 12 V/cm that is beyond the feasible range of the present device. These results demonstrate for the first time that older larvae and young adults of C. elegans respond to electric field in a liquid environment inside the microchannel and move in a directed manner.

Effect of Age on Electrotaxis

The developmental response of worms to the electric field stimulus led us to characterize it in further detail.

Figure 2:
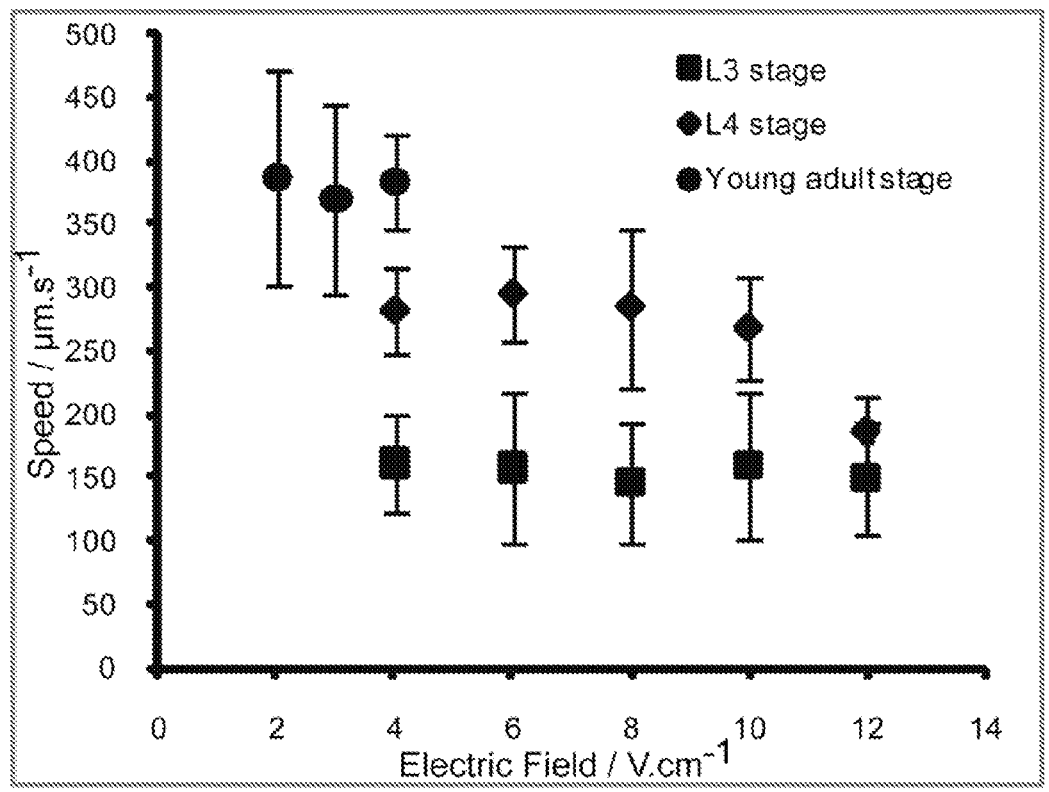
FIG. 2 graphically illustrates the effect of electric field on movement speed of different developmental stages of *C. elegans*.

At the minimum threshold electric field (2 V/cm for young adults), worms showed robust movement and oriented themselves towards the cathode. The movement of larvae and young adults was characterized as shown in FIG. 2. L3 stage worms (385-528 μm-long, dark rectangles) responded to electric fields above 4 V/cm with a speed range of 100-216 μm/s. L4 stage worms (534-725 μm-long, clear rhombuses) responded to the electric fields between 4 and 10 V/cm with a speed range of 220-340 μm/s. Due to the partial paralysis at 12 V/cm, the speed of L4 stage worms was reduced. The young adults (920-1,050 μm-long, dark circles) had the lowest effective electric field range (2-4 V/cm) since they were paralyzed above 4 V/cm. Within the effective range, their speed ranged between 296 and 471 μm/s. The upper threshold electric field was not observed for L3 stage worms due to the upper limit of allowable field without electrokinetic flow.

Figure 3:
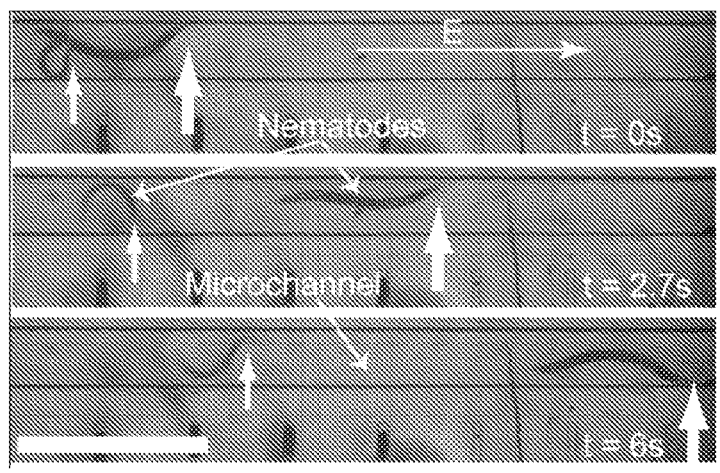
FIG. 3 illustrates separation of two *C. elegans* animals at different developmental stages on application of 4 V/cm electric field.

The results showed that the speed of individual worms at any one particular stage does not change significantly with variations in the applied electric field; however, older worms had a higher speed when compared with the younger ones (~80% increase between L3 and L4, and ~35% increase between L4 and adult). This difference in speed was effective in separating worms of two different stages as shown in FIG. 3. Separation of two animals (530 μm-long L3 stage and 1,000 μm-long young adult) within 6 seconds upon application of 4 V/cm electric field was achieved. The thin and thick white arrows mark the anterior ends of the L3 stage and young adult worms, respectively. The scale bar is 1 mm.

L3 stage animals responded to the electric field robustly starting from 4 V/cm (minimum threshold). The maximum threshold (defined by the paralysis phenotype) could not be observed because animals continued to swim normally without a change in speed even at the maximum allowable field (12 V/cm with no electrokinetic flow effect) in the channel. At later stages, animals appeared more sensitive to the electric field. Thus, while L4 stage animals were partially paralyzed at 10 V/cm (revealed by occasional abnormal body bends and reduced speed), the young adults exhibited this effect at 4 V/cm. The minimum threshold response at these two stages was 4 V/cm (L4) and 2 V/cm (young adult). Reversing the applied electric field resulted in the reversal of the worm's movement. These results demonstrate that adult animals are more sensitive to the electric field and possess the shortest response range compared to L3 and L4 larvae.

Undulatory motion of worms of different sizes was studied to determine the frequency of body bending under various electric fields using a no-field application as the witness model. It was observed that in the presence of electric field the average bending frequency of worms of different sizes (450-1,000 μm-long) (n=15) ranged between 1.7 and 2.6 Hz. The bending frequency for each worm did not change significantly (<5% variation at maximum) with a change in the electric field strength and/or direction, and it was in close approximation of the no-field movement frequency (1.78-2.52 Hz for different size animals) demonstrating that the electric field had only a minor effect on the worm's natural body motion.

Cellular Basis of Electric Field Responses in Microchannels

Figure 4:
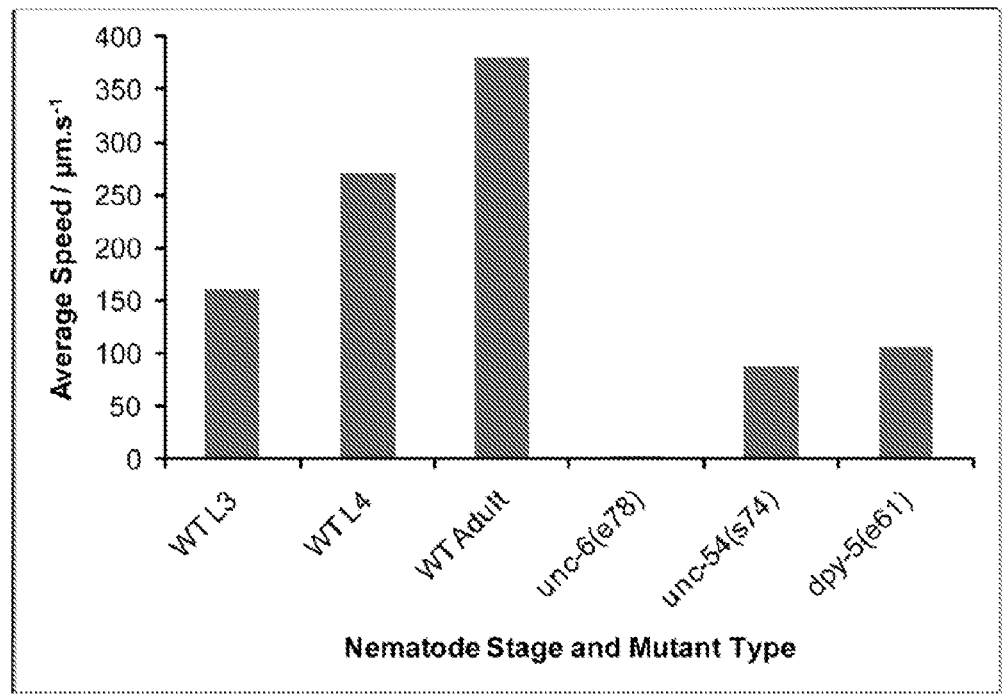
FIG. 4 graphically illustrates the average speed of various *C. elegans* animals in a microchannel on application of an electric field.

Mutant worms with defects in specific cell types were used to explore the cellular basis of electrotaxis using methods as described by Gabel et al. (J Neurosci, 2007. 27(28): p. 7586-96) and unc-6(e78) mutant animals that exhibit defects in neuronal differentiation. Studies on unc-6 have shown that it encodes a netrin-like secreted protein that plays a crucial role in neuronal growth cone migrations. The unc-6 mutant animals are uncoordinated due to defects in dorsal and ventral nerve cords. The average speed of various animals in a 5 cm-long, 300 μm-wide and 80 μm-deep microchannel was determined. The analysis of unc-6(e78) young adults in the microchannel revealed no response to the electrical stimulus and showed no obvious sign of orientation and speed change following the application of electric fields (FIG. 4).

A muscle mutant unc-54(s74) was also tested in a similar setting to determine the contribution of muscles in electric field-driven swimming behaviour. The unc-54 gene is necessary for the proper differentiation of the muscle myosin class II heavy chain (MHC B). The unc-54 mutant animals exhibit disorganized muscles and are severely uncoordinated (paralyzed). The unc-54(s74) young adult worms responded to the electric field in a manner similar to that of wild-type worms (2-4 V/cm range) although their speed was significantly slower (unc-54: 88 μm/s, wild type: 380 μm/s, average speeds) (FIG. 4). This is interesting considering that unc-54 (s74) worms on standard culture plates (NG agar) exhibit almost complete paralysis. These results indicate that the electrosensory response in microchannels is primarily mediated by neuronal activity.

Sensitivity of Electric Field Response: Size Vs. Development

The experiments revealed that adult worms respond to electrical fields much more robustly compared to younger (L3 stage) animals (FIG. 2). Considering that electrosensory behaviour is mediated by neurons, it is possible that adult worms have a mature nervous system and are therefore capable of processing neuronal signals more efficiently than the younger developing worms. Such a difference may also result from a change in the length of worms since adult worms are significantly larger compared to L3 stage animals (~1,000+/−100 µm and ~450+/−100 µm, respectively).

To distinguish between these possibilities, two different mutant strains that are shorter (dpy-5(e61)) and longer (lon-2(e678)) as compared to wild type were studied. The dpy-5 gene encodes a collagen that is necessary for the cuticle formation in developing larvae whereas lon-2 encodes a glypican family of heparan sulfate proteoglycans that negatively regulates DBL-1/BMP signaling to control body length. Mutations in these two genes give rise to opposite phenotypes. Thus, while dpy-5 mutant animals are approximately 60% shorter compared to the wild type (400+/−100 µm and 1,000+/−100 µm at 62 hours, respectively), the lon-2 mutant animals are roughly 30% longer (1,300 µm+/−100 µm at 62 hours) than wild type. Both these mutant animals are otherwise healthy and active.

The analysis of dpy-5(e61) animals in the microchannel revealed that, unlike wild type animals (effective response range of 2-4 V/cm), these animals responded to the electric field robustly starting from 4 V/cm and showed no sign of paralysis at the highest possible field tested (12 V/cm). Their average speed (106 µm/s) did not change in response to an alteration in the electric field strength and/or direction. In contrast, the lon-2(e678) animals did respond to the lowest threshold electric field like wild type (2 V/cm). However, these animals appeared extremely sensitive and were paralyzed under the influence of electric fields higher than 3 V/cm. Due to their larger size, they were unable to move freely in the microchannel and exhibited abnormal movements. This precluded measure of their speed. These results demonstrate that longer worms are more sensitive to electric field than shorter worms indicating that size is a major determinant of the sensitivity of C. elegans to the electric field. This was most likely due to differences in the potential drop across the entire body that is greater in lon mutants compared to wild type (~30%). This may also explain the variability in responses observed for different stages of wild type animals since they are not exactly alike.

Post-Exposure Effect of Electric Field

Considering that worms appeared paralyzed when exposed to electric fields greater than their response range, the post-exposure effect was determined by examining behaviour, fertility and viability. For this, 10 adult animals were aspired into the channel individually and a constant electric field (2-4 V/cm) was applied across the channel for duration of 10 minutes. During this period, the polarity of the field was reversed every minute (while keeping the field strength constant) in order to keep the worm inside the channel and to prevent it from getting in direct contact with the electrodes. In one case, a young adult worm was exposed to 12 V/cm electric field (three times that of maximum threshold electric field of wild type animals) for a duration of 10 minutes. Following electric field exposure, worms were removed and grown on standard culture plates. In all cases (n=11), animals recovered successfully within a few hours, exhibited normal sinusoidal pattern of movement (i.e. no uncoordinated movement), did not die prematurely (~18 days average age), and were fertile for 3-4 days (similar to unexposed wild type worms). This demonstrates that the electric field stimulus causes no visible harm to C. elegans and that there are no long-term developmental and behavioural changes following exposure.

Thus, C. elegans behaviour in a microfluidic environment was studied in the presence of a low voltage electric field and was determined to be useful as an attractant to guide their movement without physiological and behavioural side effects. Application of electric field in worms induces forward movement towards the cathode that is robust, highly reproducible, and sensitive.

The electric field response was measured in microchannels at a range of electric field strengths (with minimum and maximum thresholds) within which an optimum electrotactic response was observed. Not all stages of animals responded equally well within the same threshold range. Thus, while the effective range for L4 larvae was 4-10 V/cm, adults appeared significantly more sensitive and had a lower response threshold (2-4 V/cm). Within the optimum range at any given stage, the speed of movement of animals remained unchanged suggesting that the electric field response is a binary phenomenon (all or none). All responding stages of animals (L3, L4, and young adult), when exposed to the electric field above the maximum threshold, exhibited paralysis as judged by their near rod-like shape and abnormal body bends. This effect was reversible since the animals resumed normal movement upon lowering the electric field. Furthermore, it was demonstrated that the electric field manipulation of C. elegans does not appear to be harmful since the exposed animals, when placed on standard culture plates, resumed normal movement and feeding behaviour and continued to reproduce normally.

The cellular basis of electrotaxis in a liquid environment was also found to be neuron-dependent. Thus, unlike previously described pneumatic microdevices that rely on forced liquid flow to move worms, the use of the electric field stimulus in the present assay induces a very precise and sensitive innate movement response.

EXAMPLE 2

DC Electrotaxis of C. briggsae

It was also determined whether or not electrotaxis is a conserved process between C. elegans and its cousin species C. briggsae. C. briggsae is very similar to C. elegans in terms of morphology, development, and genetic makeup. C. briggsae worms (n=5, 845±40 µm length, 62 hr YA) were tested under DC electric fields (1-6 V/cm) in a similar manner to C. elegans. All tested animals responded to the electric field and moved towards the cathode spontaneously after the application of the signal. The entire movement response was recorded and analyzed as described previously (Rezai et al. Appl Phys Lett, 2010. 96(15): p. 153702.6).

Figure 5:
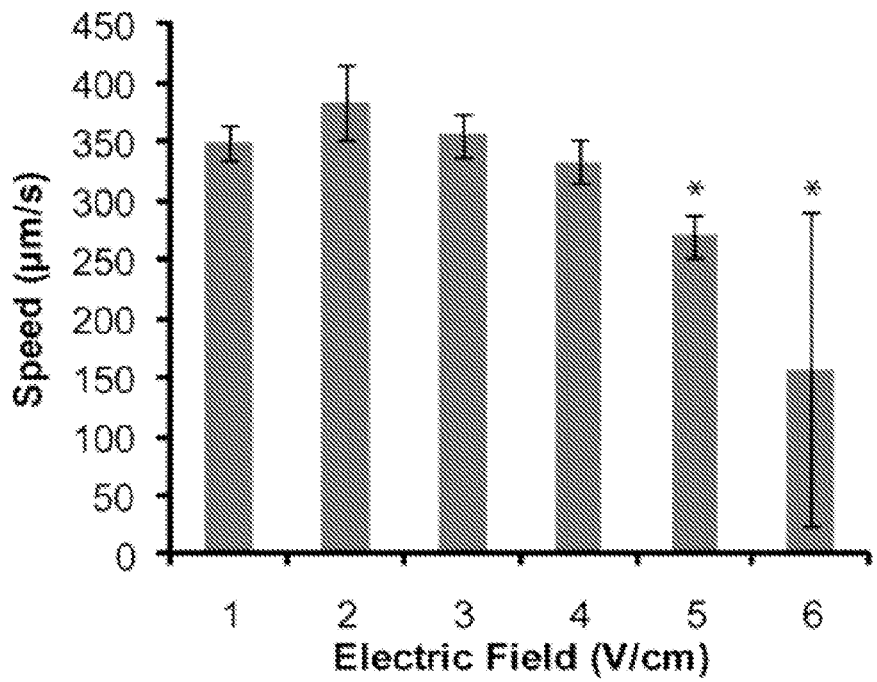
FIG. 5 graphically illustrates DC electrotaxis speed of *C. briggsae* at various electric field strengths.

It was observed (as shown in FIG. 5) that C. briggsae responded to electric fields in a range of 1-4 V/cm and showed partial paralysis starting at 5 V/cm. Consistent with this, the electrotactic movement speed at 5 and 6 V/cm was significantly lower compared to 1-4 V/cm ($p<0.01$, ANOVA). The paralysis was initially observed in the tail region as animals appeared to gradually form coiled-shape configuration in the tail region which extended to the whole body if the signal persisted, eventually leading to coiling. Although the higher threshold of response (4 V/cm) of young adult C. briggsae was similar to that of C. elegans, it was observed that these animals, unlike C. elegans (which had 2 V/cm lower threshold), responded to DC electric fields as low as 1 V/cm in a robust manner (100% responders, n=5). However, similar to C. elegans, swimming speed of C. briggsae did not vary significantly with electric field strengths in the active range (1-4 V/cm) (p>0.01, ANOVA) and had an average value of 356±20 µm/s. The *C. elegans* (n=7, 719±37 µm length, 62 hr young adult) DC electrotaxis experiment was repeated and an average speed of 296±43 µm/s in the 2-4 V/cm range was observed. The body stroke frequency for both *C. briggsae* and *C. elegans* was on average 2±0.1 Hz, resulting in slightly higher speed for *C. briggsae* (FIG. 5).

EXAMPLE 3

AC Electrotaxis of *C. Elegans*

Figure 6:
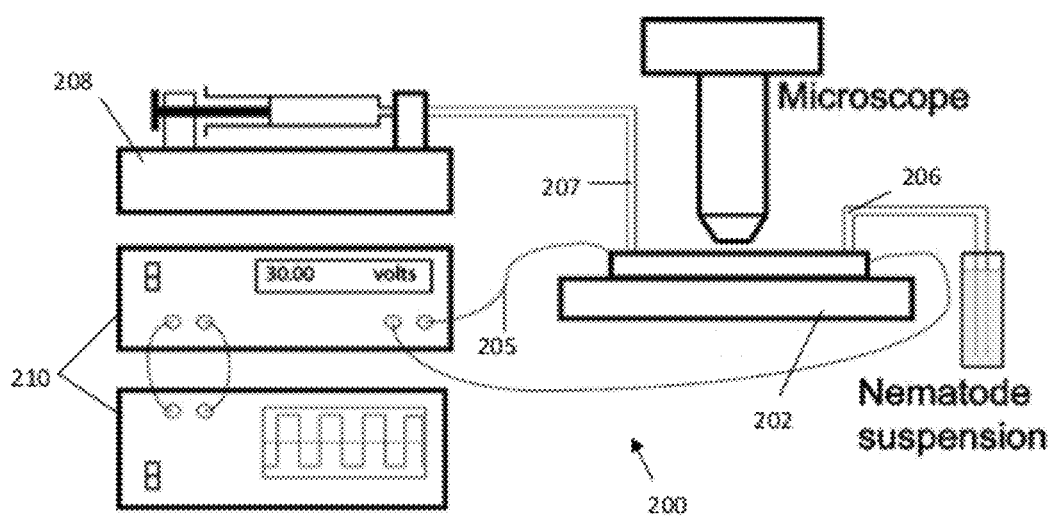
FIG. 6 illustrates an electrotaxis device useful to study electrotactic response to AC electric field.

Although worms can be stimulated to travel along an intended direction using the DC electric field, they cannot be held in one place. As localization is an important control mechanism for high throughput automated handling of worms in a microfluidic channel, the use of alternating (AC) electric field to localize *C. elegans* in microchannels for an extended period of time without any physical confinement was tested. An AC electrotactic device 200 was used to study the effect of AC field on worms is illustrated in FIG. 6. The device 200 consists of a microchannel component 202 (e.g. 5 cm-long, 300 µm-wide, and 80 µm-deep) comprising a reservoir 204a, 204b formed at each end connected by a channel 205 marked with a length scale. An inlet 206 feeds into one reservoir 204a from a sample holder (e.g. worm sample), while an outlet 207 extends from the second reservoir 204b and is connected to a syringe pump 208. Electrodes 209 and 210 (cathode 209 and anode 210) were embedded at both reservoirs and connected to a power supply unit 212 (an electric signal generation, e.g. amplifier and function generator) that applies different waveform AC electric fields. The microchannel 202 was constructed of polydimethylsiloxane (PDMS) pre-polymer using soft lithographic and contact printing methods as described above.

Figure 7:
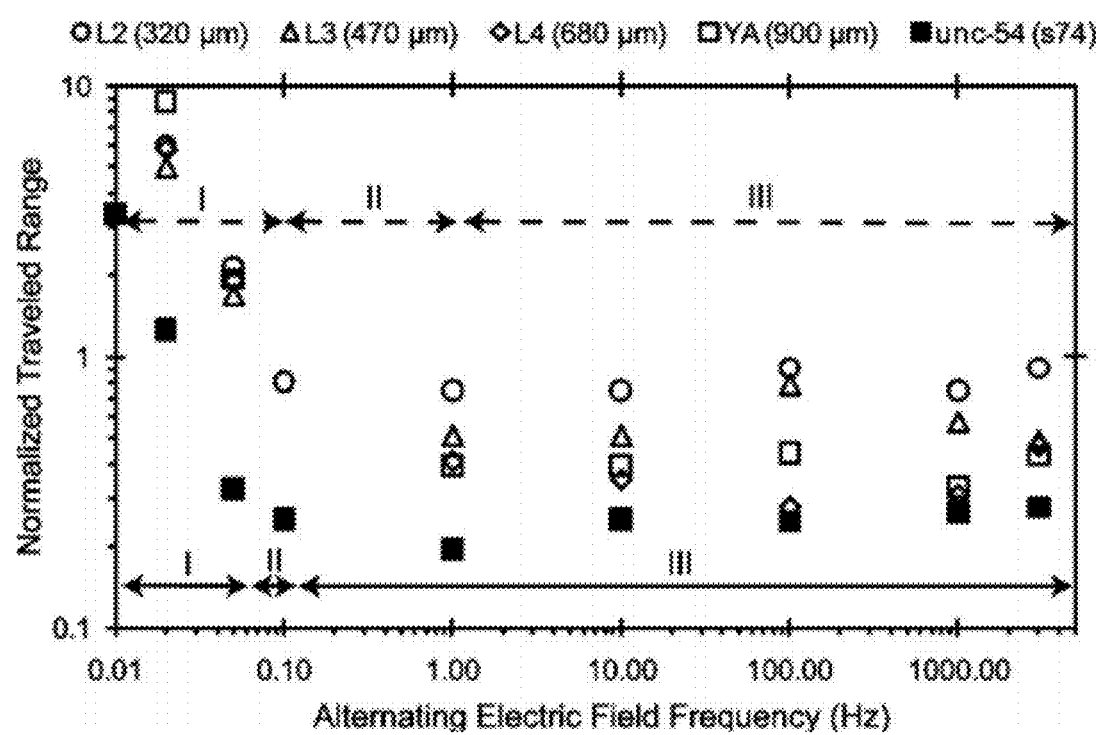
FIG. 7 graphically illustrates the AC electric field response of various *C. elegans* animals.

Worms were loaded individually into the microchannel 202 using a syringe pump 208 and placed in the middle (2.5 cm away from each electrode). A constant DC electric field was applied across the channel to stimulate animals to initiate swimming towards the cathode for a short distance (3 mm). Afterwards, an AC electric field with square waveform (frequency between 20 mHz and 3 KHz) was applied and the response of animals was recorded using a camera. Results are shown in FIG. 7. Normalized traveled range (Traveled Range/Average stage length) decreases with frequency increase for all stages. Regions I, II, III correspond to DC-like electrotaxis, 1-directional movement, and localization frequency range respectively, illustrated for wild type (dashed double side arrowed lines) and muscle mutant nematodes (solid double side arrowed lines). Applied electric field was 10, 8, 6, and 3 V/cm for L2, L3, L4, and young adult (YA) stages respectively. Average length for each developmental stage is as follows: L2 (320 um), L3 (470 um), L4 (680 um) and YA (900 um).

At low frequencies (between 20 and ~100 mHz), L2 and older stage animals moved in one direction (towards the cathode) in the positive half of the cycle and reversed their direction (towards cathode) in the negative half of the cycle (portion I in FIG. 7). The distance traveled during each AC field half-cycle before direction reversal was measured and dubbed as "traveled range". The traveled range data (shown in FIG. 7) was normalized using the average length of nematodes tested at each developmental stage (n=10 for each stage). At frequency ranges between ~100 mHz and ~1 Hz, the nematodes swam in the following pattern (termed "stop and go"). When the polarity of the AC electric field coincided with the direction in which they were initially travelling, the animals continued to move in that direction. Interestingly, field reversal (during the other half cycle) did not alter their direction of travel. The animals were either momentarily localized or their speed was severely reduced. Subsequently, in the next cycle, they continued their forward motion. This demonstrates that although the nematodes are able to sense the field reversal, they are unable to reverse their movement direction (1D movement shown as portion II in FIG. 7). At higher frequency ranges (~1 Hz-3 KHz), young adults were almost completely localized in the channel, with movement being restricted to an average distance of 0.41 of their body length (See portion III of FIG. 7). It appears that the frequency of signal switching is just enough for worms to sense the direction, but before they could initiate movement, the direction of the field had reversed. Consequently, the animals were unable to move at all. The nematodes stayed localized in the channel for the entire duration of the AC electric field, with no or a few rotations. Subsequent application of the DC electric field induced them to move towards the cathode. To illustrate the localization behaviour inside the microfluidic channel, worms were transported using the DC electric field to a desired location inside a channel, localized using AC electric field for a specific duration of time (20 s) and then subsequently transported away using the DC field. These results demonstrate that a combination of DC and AC electric fields could be used to efficiently guide and localize worms in a microfluidic channel without the use of physical constraints (such as the vacuum suction).

Synchronized worms of various ages (L1 stage to young adult stage) were tested using the same square waveform and frequency range. The results are shown in FIG. 7. All developmental stages (except for L1 stage) responded to the AC electric field in the same manner as young adults but with a slight variation in their range of localization. All stages demonstrated decreased traveled range with increase in frequency. Frequencies above ~1 Hz appeared to localize worms but as shown in FIG. 7, older animals responded more robustly to the AC electric field (average normalized traveled range of 0.41 for young adults and 0.91 for L2 stage for f≥1 Hz). For the older animals, more instantaneous responses to the AC electric field compared to the younger ones was observed. For example, some L2 and L3 stages (n=4 out of 20 total) exposed to the frequencies above 1 KHz failed to respond instantaneously and traveled for a short distance (<1 mm) before being localized. This phenomenon was not observed in L4 and young adult stages that were localized immediately upon AC electric field application. All stages that showed a response exhibited a few or no rotations at the point of localization, although shorter worms (L2 stage) preferred to orient their body perpendicular to the axis of the microchannel.

The effect of sinusoidal and triangular AC signals on young adult stage worms in frequency ranges above 1 Hz (localization range) was tested. The response of animals was found to be the same as with square waveforms. Square waveforms with varying duty cycles (1% up to 80%) were also tested on young adults to minimize the electric field exposure time while preserving the localization effect (data not shown). Even 1% duty cycle signals localized the worms in the same manner as square waveforms reducing the exposure time by 99%.

In addition to wild type, young adult worms with defective body wall muscles (unc-54(s74) mutant) were tested for their response to square AC electric field. The animals showed AC and DC electrotaxis but since they had considerably lower mobility compared to wild-type animals, even less average normalized traveled range (0.25) and reduced localization frequency range (100 mHz-3 KHz) was observed.

Thus, control of the movement of *C. elegans* in a microfluidic environment using AC electric field as a stimulus has been exhibited. Since movement is controlled by neurons and muscles, this discovery holds promise in the development of microfluidic-based high throughput assays to study and manipulate these two cell types in worms. The ability to induce movement in a desired direction (using DC electric field) and to localize animals at a specific location (using AC electric field) can be very useful in various applications. Incorporating a method of movement-based microfluidic assays is useful to study diseases, screen for drugs, and examine their mechanism of action in *C. elegans*.

EXAMPLE 4

Pulse DC Electrotaxis of *C. elegans* and *C. briggsae*

The device 200 used to perform these electrotaxis experiments on worms in FIG. 6 and comprised a PDMS microchannel 202 (e.g. PDMS channel 100 µm-deep, 300 µm-wide, and 50 mm-long) with wire electrodes 205 and fluidic inlet 206 and outlet 207 access tubes inserted at its end reservoirs. The outlet tube 207 was connected to a syringe pump 208. Soft lithography technique was utilized for the fabrication of the microchannel 202 in polydimethylsiloxane (PDMS) material. The electrodes 205 were connected to an electric signal generation unit 210 (comprising a function generator and amplifier) for the application of electric fields and hence currents in the channel. This unit consisted of a AFG3022B function generator (Tektronix Inc., OR, USA) with a maximum voltage output of 5 V, a 677B amplifier (TREK Inc., NY, USA) with a 400 gain, a custom made simple switch to reverse the polarity of electrodes, and copper wires to connect the setup to the device electrodes.

Generation of Electric Field

Figure 8:
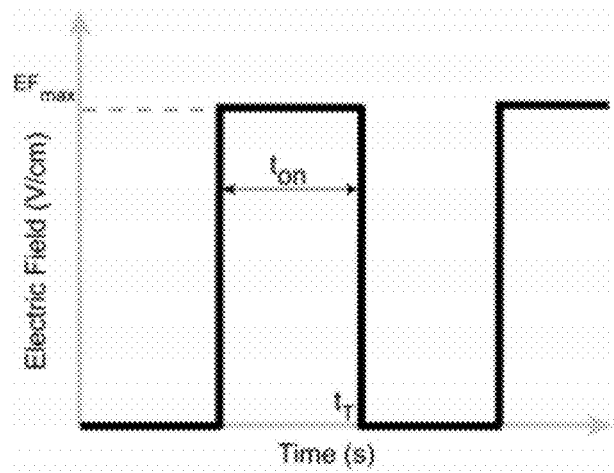
FIG. 8 shows the Pulse DC electric field signal waveshape.

The function generator was set to output a pulse DC electric field with adjustable characteristics such as the frequency ($f=1/t_r$), maximum pulse electric field strength ($EF_{max}$), as well as the duty cycle calculated using equation (1). The waveform of the pulse DC signal is shown in FIG. 8. The signal rises in a step-like manner from zero to a maximum set point for a controllable duration of time (duty cycle) and decays to zero for the rest of the signal cycle which is then repeated at a fixed frequency.

$$\text{Duty Cycle (\%)} = f \times t_{on} \times 100 \quad (1)$$

where $t_{on}$ is the on-portion time of the pulse signal. Since the maximum pulse electric field strength ($EF_{max}$) output of the function generator did not exceed 1 V/cm, the signal was subsequently amplified and applied to the microdevice. The rise and decay time of the pulse signal were 50 µs each, which restricted the experimental frequency range to less than 1 kHz and the duty cycle to more than 10% in order to produce a rectangular-shape pulse waveform.

Animal Culture and Maintenance

The *C. elegans* N2 and *C. briggsae* AF16 strains were grown on standard NG agar plates previously seeded with OP50 strain of *Eschericia coli* and maintained at 20° C. Synchronized worms were used in all the experiments. For this, gravid adult hermaphrodites were treated with bleach solution (commercial bleach and NaOH (4N) in the ratio of 3:2). After bleach treatment, dead worms were washed with M9 solution (3 g KH2PO4, 6 g Na2HPO4, 5 g NaCl, 1 ml MgSO4 (1M) in 1 liter). Embryos were hatched in M9 following 24 hours incubation such that hatched worms were arrested at L1 stage. The animals were plated on NG agar plates and grown till they reached adulthood.

For all experiments, synchronized worms were individually loaded into the microchannel from a reservoir of diluted worm suspension (in M9) and positioned at the center of the channel by applying suction at the outlet. The inlet and outlet tubes were then leveled to the same height to prevent any flow in the channel. The head orientation of the worm was then determined in the microscope. The worms moved randomly in either direction (left or right) or remained stationary within the channel. The electric field (either constant or pulse DC) with a specific duty cycle and frequency was then applied along the channel (parallel to worm's body) in a direction opposite to its head orientation. The resulting movement response was digitally recorded using a camera (Coolpix P6000, Nikon Inc., Tokyo, Japan) connected to the microscope for the entire duration of the experiment. The applied stimulus either forced the worm to turn inside the microchannel and move towards the cathode at its rear or did not generate any response. For the responding worms, forward motion speed under signal application and turning time under signal reversal were measured from the video as behavioural phenotypes. Since there was a large variation in turning response time between individual worms in the case of pulse DC signal, and to identify the responding worms after each field reversal, the worm was allowed to sense the signal reversal and initiate a turn response for up to 40 s immediately after the signal reversal. The worm was considered either a responder, if it turned within the given time window, or non-responder, if this time elapsed without a turn. The aggregate population response time was then used for data analysis. The turning time data was recorded for different durational intervals (i.e. 5, 10, 20, and 40 s). The responder worms were allowed to swim towards the cathode for a distance of 5 mm after which the polarity of the electrodes across the channel was reversed and the worm's behaviour was recorded. This process was repeated thrice for each animal to rule out a random electrotactic turning response. In the case of non-responding worms in the 40 s time window after signal reversal, the field was switched off, the worm was delivered to the center of the channel again pneumatically, and the same experiment was repeated two more times. The signal characteristics (either frequency or duty cycle) were then set to a different value and the experiment on the same worm was repeated for the desired spectrum of frequency (1-1000 Hz) and duty cycle (10-90%). After this set of experiments, the worm was washed off the channel.

Results and Discussion

Two different movement phenotypes i.e. turn time after signal reversal and forward motion speed during signal application, were studied. The results were compared to DC electrotaxis of these animals and are described below.

Figure 9:
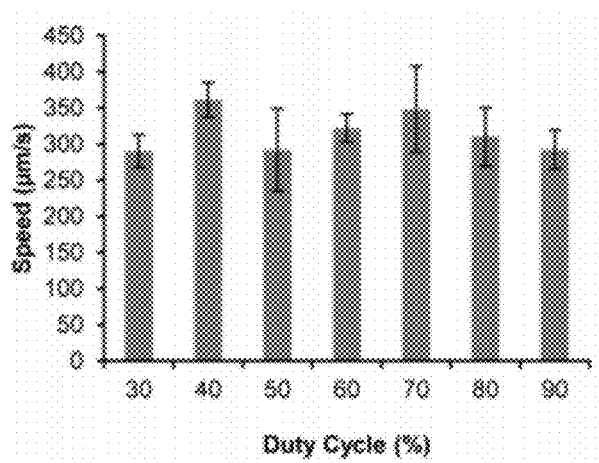
FIG. 9 graphically illustrates the effect of duty cycle on *C. elegans* pulse DC electrotaxis forward motion speed.

With a pulse DC signal, the duration of the electric field stimulation of the worm can be adjusted by changing the duty cycle of the signal as shown in FIG. 9. In addition, this method has the potential to provide information about the response time of a population of worms to electrical signals. For instance, if the pulse width of the signal is below the response time of the animal, then that signal will not elicit a movement response even when an indefinite number of cycles of this signal is applied. In this experiment, *C. elegans* and *C. briggsae* worms (62 hr young adults) were loaded individually into the channel. The time for the worms to turn around in response to reversal of the pulse DC signal, at various duty cycles, were recorded for a population of worms. Simultaneously, the speed of worms in response to pulse DC signal at various frequencies and duty cycles was also recorded. For all pulse DC experiments, the maximum electric field of the pulse signal was set to $EF_{max}=3$ V/cm.

Figure 10:
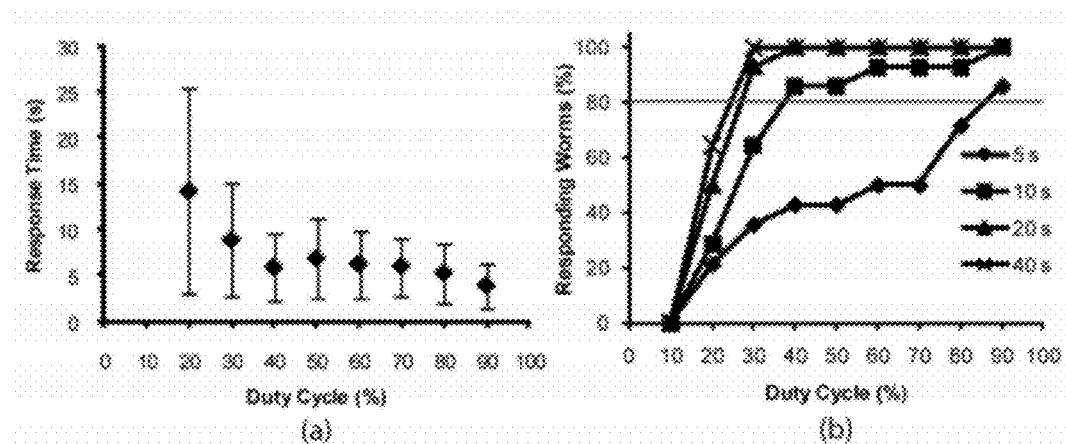
FIG. 10 shows the effect of duty cycle on *C. elegans* pulse DC electrotaxis turn response time (a) and percentage of responders (b)

In order to examine the effect of the duty cycle on electrotactic response, C. elegans worms (n=14) were exposed to a range of duty cycles (from 10% to 90%) at a constant frequency of 1000 Hz and their forward motion speed was analyzed (FIG. 10a) and turning response time (FIG. 10b) to the directional change of the signal. The speed of the worms remained constant with average values between a minimum of 290±37 µm/s and a maximum of 360±24 µm/s at different duty cycles (30%-90%, robust response range shown in FIG. 10b) as shown in FIG. 10a. These average speeds were statistically independent (p>0.1, using a single factor analysis of variance method, ANOVA) of duty cycle values and were averaged at 315±37 µm/s. This result indicates that even when the electrical stimulus is not continuous, it is sufficient to induce movement response in the worm. The turning response of the worms to DC and pulse DC signals was examined when they were reversed suddenly. Here, the worms were exposed to a constant or pulsed DC signal (with specific duty cycle at a fixed frequency of 1000 Hz) that was reversed suddenly. The turning time of the worm was then measured as described in the experimental section. The signal reversal was repeated twice to confirm that the turning response was genuine. The average turning time for a 3V/cm DC electric field was measured to be 6.6±2.6 for 100% of responder YA worms. However, the time for the worms to turn around in response to pulse DC signals varied significantly (FIG. 10a) for certain duty cycles even though the experiments were done on a homogenous population of young adults. This variation in response time was greatest when the duty cycle was the smallest (large standard deviations at low duty cycles in FIG. 10a) and was reduced as the duty cycle increased and the signal approached constant DC. In addition to this, a lesser number of worms responded in the 40 s window at very low duty cycles. For instance, no worm responded at 10% duty cycle in less than 40 s and the turn response was first observed at 20% duty cycles. In order to understand this data better, population statistics was used as shown in FIG. 10b, which plots the percentage of worms that responded to the pulse DC signal (at 1000 Hz frequency) of a certain duty cycle in a specific time window (i.e. 5, 10, 20 and 40 s). At lower duty cycles, comparatively fewer worms responded quickly to the reversal of the pulse DC signal. For instance, only 20% of the worms responded to 20% duty cycle signal with a turning response time of 5 s or less. However, 60% of them were able to respond to the change in direction within 40 s. Thus, as the duty cycle of the signal was increased, an increasing proportion of the worms responded to the signal in a faster manner. For instance, the proportion of the worms responding to the reversal of signal within 5 s increases from 20% at 20% duty cycle to ~80% at 90% duty cycle. At lower duty cycles, the majority of worms responded later to the field reversal and their turning time was prolonged. This phenomenon could be related to the time required for the polarization of the neurons that mediate the movement response. This variation in duty cycle of pulse signals and turning response time to field reversal together provide a unique method to elicit varying movement response to correspondingly varying electrical stimulus.

Figure 11:
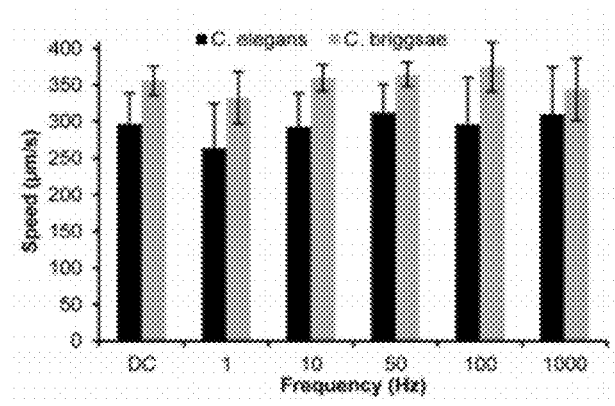
FIG. 11 graphically illustrates the effect of frequency on *C. elegans* and *C. briggsae* pulse DC electrotaxis forward motion speed.

The effect of the frequency of pulse DC signal on the forward-motion electrotactic movement speed was also studied for C. elegans. A duty cycle of 50% that induced robust response in worms (more than 80% responders in less than 10 s in FIG. 10b) was used for the pulse DC field with frequencies ranging between 1-1000 Hz. The speed of the electrotactic forward movement is shown in FIG. 11. Each data point corresponds to an average of 7 worms (62 hr young adult, 719±37 µm long) examined. Average DC electrotactic speed of these animals is also depicted in the same figure for comparison.

It can be seen clearly that the frequency does not have a significant effect on the pulse DC forward electrotactic movement speed (p>0.1, using ANOVA) which was similar to their DC electrotactic movement speed. The C. briggsae worms (n=7) responded in a similar fashion (FIG. 11), indicating that the mechanism of electrotactic response is conserved between the two species.

Figure 12:
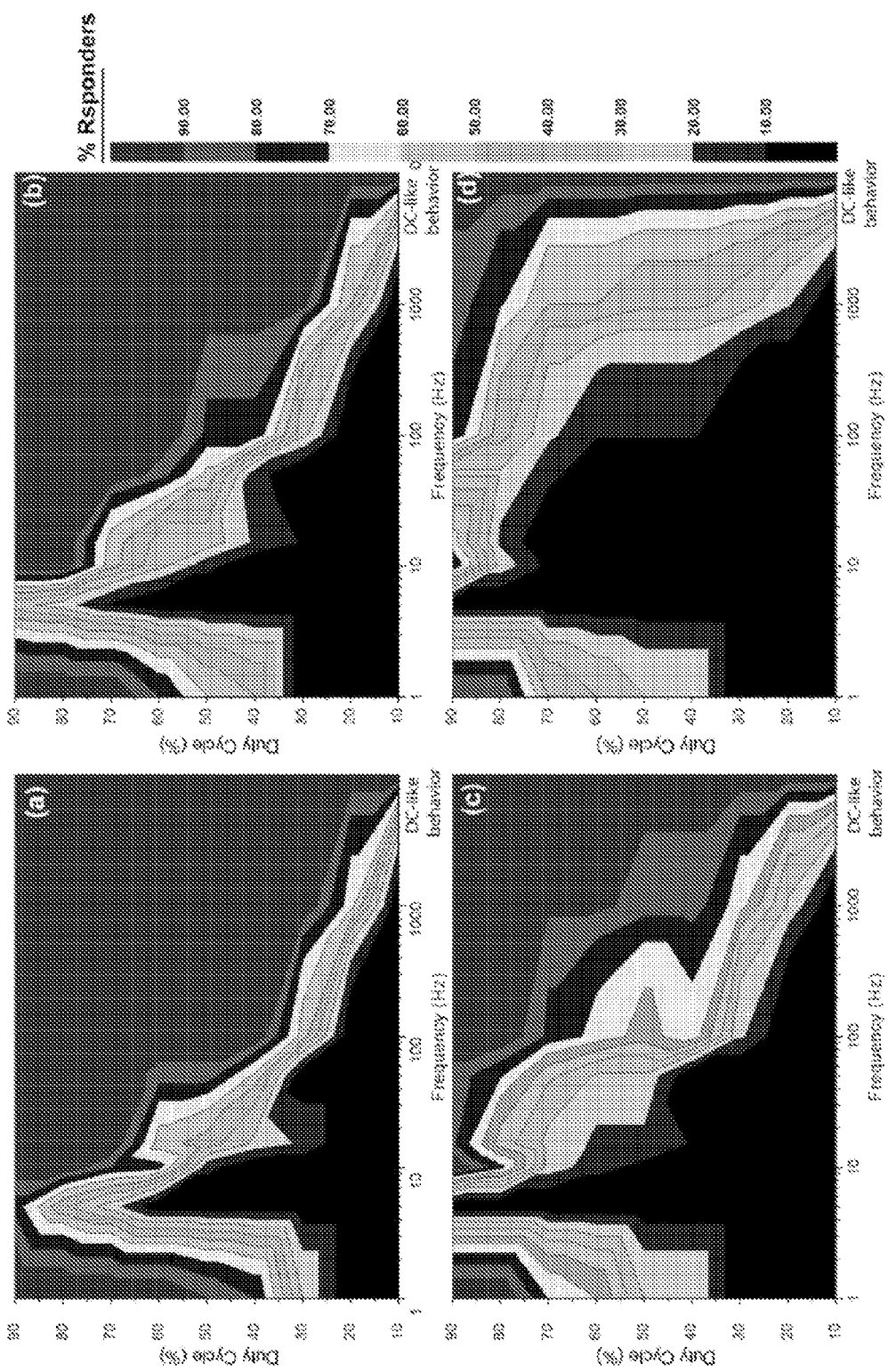
FIG. 12 shows the percentage of responding *C. elegans* in less than (a) 40 s, (b) 20 s, (c) 10 s, and (d) 5 s, to pulse DC electric field at different frequencies and duty cycles.
Figure 13:
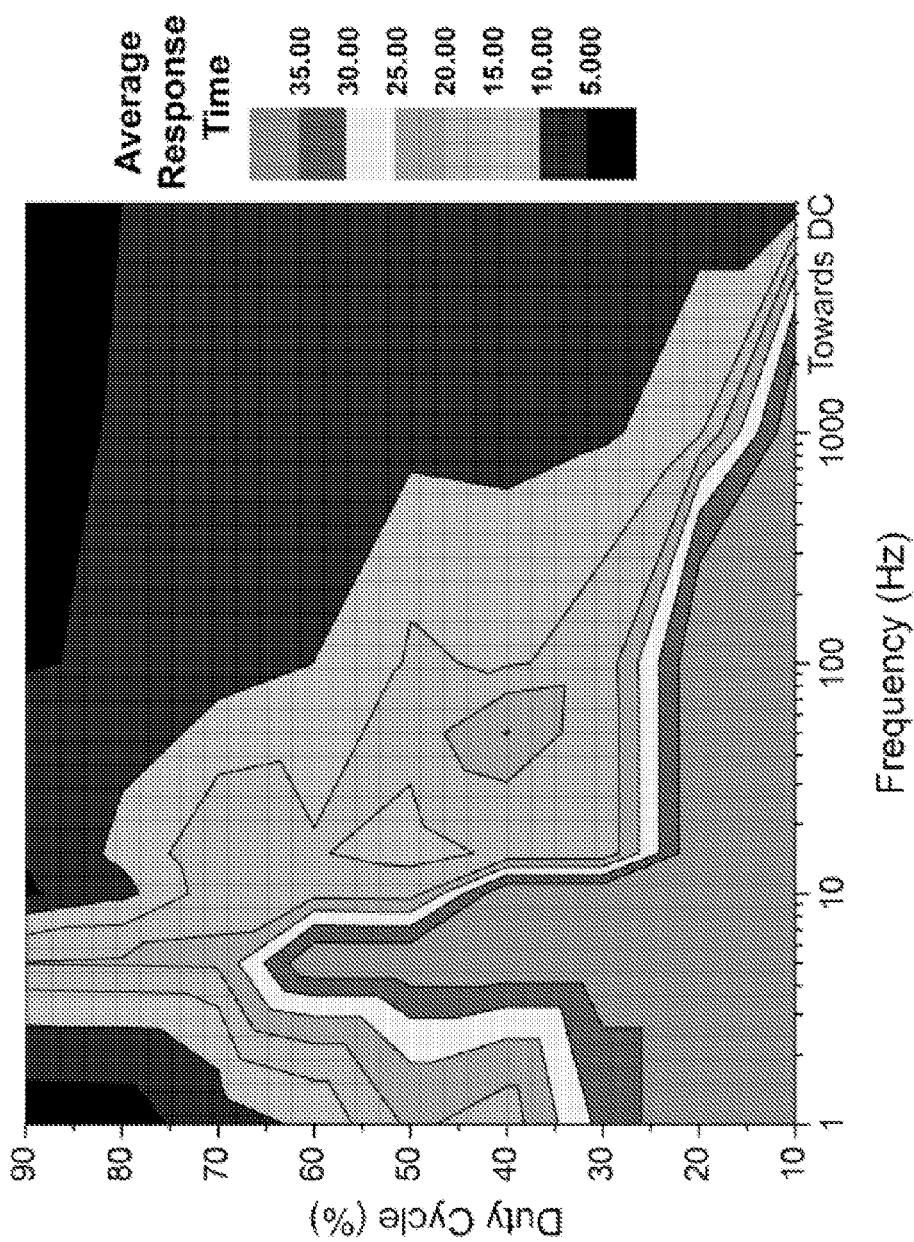
FIG. 13 shows the average response time of adult worms to pulse DC electric fields at different frequencies and duty cycles.

It was shown that for robust (>80% responders) pulse DC electrotaxis, a minimum duty cycle at 1000 Hz frequency level was used. The effect of different frequencies on turning behaviour of C. elegans was also studied to assess the number of responders at different times (FIG. 12, tR=40 s (a), tR=20 s (b), tR=10 s (c) and tR=5 s(d)) and their average response times (tR) (FIG. 13). According to FIG. 12, the number of worms responding at each pulse DC frequency level increased with increase in duty cycle from 10% to 90%. On the other hand, at a specific duty cycle, the highest number of worms responded at higher frequencies. However, this increasing response was not linear. In fact, the number of responders decreased from f=1 Hz to f=5 Hz at all duty cycles and then increased as the frequency was raised. Even at 90% duty cycle at f=5 Hz, less than 10% response was observed in tR<10 s (FIGS. 12c and 13). At f=5 Hz, only ~20% of the worms responded in between 10 s to 20 s to 80% duty cycles (FIG. 12b) and an additional 20% of them responded in 20-40 s (FIG. 12a). All other frequency levels at 80% duty cycle saturated to 100% worm response (FIG. 12) and an average response time of $\bar{t}_R \leq 20$ s (FIG. 13) to the field. It can also be seen that the response becomes more similar to DC electrotaxis as the frequency increases to 1 kHz (FIG. 13). In addition, fast and robust response happens either at high frequencies with low to high duty cycles or at f≤1 Hz but duty cycles of 50% and above.

This technique can be used to precisely study the turning behaviour of nematodes and the neurons and genes involved in this behaviour.

EXAMPLE 5

Microfluidic Components—Integrated Electrodes

For the development of electrotaxis-based high-throughput screening (HTS) assays, integrated microelectrodes for actuation and control of worm transport and integrated sensors for position identification and feedback have been designed. The worms have short time adverse reaction to high electric field gradients and to contact with the electrode while exposure to ionic currents in the microchannel is benign.

The present integrated microelectrodes do not interfere with the normal behaviour of the worm. One approach is to microfabricate hydrogel coated metallic electrodes so that the worms are exposed to only ionic currents. Various methods to integrate the hydrogel with electrodes, such as photolithographic based microfabrication, and to construct gel-filled microchannels as electrodes are possible. In another approach, we can use liquid electrodes and its effect on the viability and behaviour of the worms. Liquid electrodes consist of microchannels filled with highly conductive liquids and gels such as polyelectrolytes, polyelectrolyte gels and agarose gel, and interfacing with the main microfluidic channels through a high density nanoporous membrane, e.g. a polycarbonate porous membrane, that effectively transmits ionic current and potential into the channel but prevent transport of biological material across it. The effect of pore size and pore density (e.g. a pore size of 1 to 5 micrometers and density of $2 \times 10^7$ to $4 \times 10^5$ pores/cm$^2$, respectively) on the electric field distribution may be optimized to design a suitable electrode that imposes electric field but does not affect the functioning of the worms or the assay in any way.

We have also designed electrical methods for detecting the position and location of worms that is simple and can be multiplexed and suited for HTS. This is necessary in a number of unit operations described below. The sensing will be done by measuring the impedance of the microchannel cross section using electrodes that are embedded in the bottom surface of the microchannel. The impedance measurement depends on the permittivity of the fluid filling the microchannel. When the worm enters the domain over which impedance is measured, it changes the overall permittivity of the gap and this event can be recognized by change in the impedance signal.

EXAMPLE 6

Microfluidic Sorters

A microfluidic sorter has been designed to obtain highly synchronized populations of animals with similar electrotactic response. The use of synchronized populations is necessary in chemical screening methods in order that chemical exposure is the primary determinant in the change in the electrotactic behaviour, thereby increasing the confidence and sensitivity of the assay.

Figure 14:
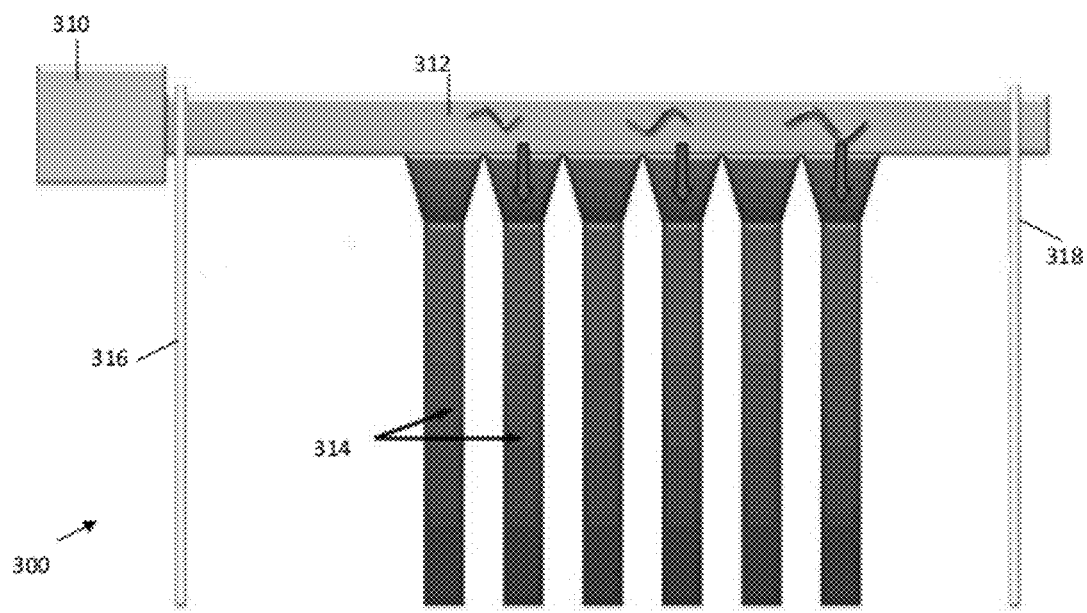
FIG. 14 shows an electrotaxis-based separation device for selecting *C. elegans* worms with identical electrotactic response.

As shown in FIG. 14, a microfluidic sorter 300 is provided. The sorter 300 comprises a worm reservoir 310, a separation channel 312 and a series of collection channels 314 which extend perpendicularly from the separation channel at various lengths across the separation channel 312. An accumulation electrode 316 is positioned adjacent to the reservoir 310 at the proximal end of the separation channel 312, and a separation electrode 318 is positioned at the distal end of the separation channel 312.

Figure 15:
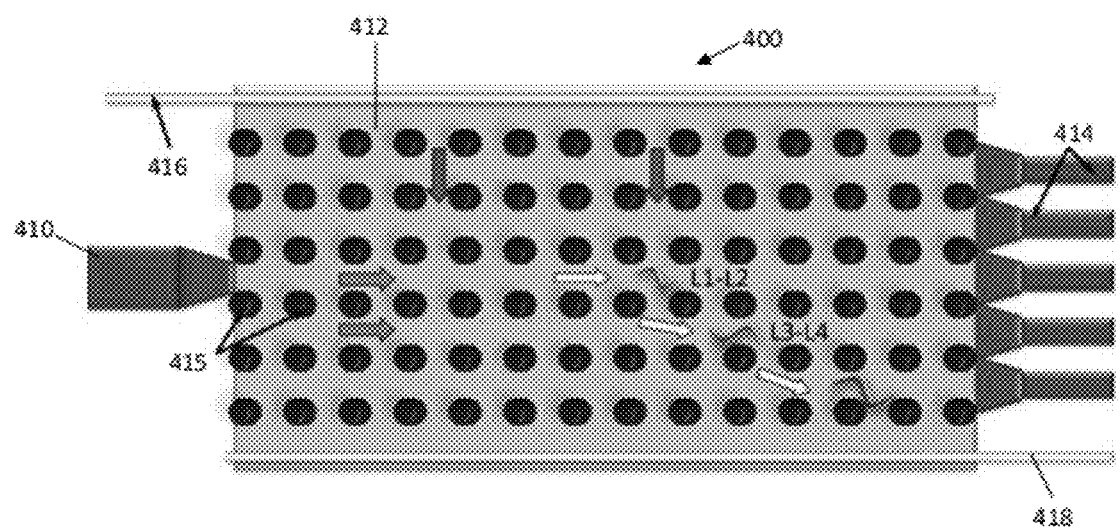
FIG. 15 shows a field flow fractionation device for *C. elegans*.

The sorter 300 separates worms into sub-groups based on electrotactic response to a constant electric field. The worms were loaded into the reservoir 310. An electric field (cathodic potential) was applied to the accumulation electrode 316 to collect the worms. Once a sufficient number of worms accumulated, the polarity was switched and the separation electrode attained cathodic polarity. The worms then moved along the separation channel at various speeds based on their electrotactic response. Once sufficient separation was been achieved, electric field was applied in the perpendicular direction via collection electrodes within the collection chambers to move the iso-electrotactic sub-groups into individual collection channels 314. Separation of worms based on their size and electrotactic response in a microchannel was achieved using this sorter In another embodiment, as shown in FIG. 15, continuous field flow fractionation-type separation sorter 400 is provided. In this sorter 400, electric field is applied in a direction perpendicular to the direction of worm movement in a pressure driven flow. Depending on the range of electric field applied and the electrotactic response of the worms, they are fractionated into sub-groups continuously. The sorter 400 comprises separation channel 412 having an inlet 410 at its proximal end and collection channels 414 at its distal end. Worms enter into the separation channel 412 at inlet 410 via a pressurized flow (10-15 μl/min) Separation electrodes 416 and 418 are positioned at either side of separation channel 412 and function to provide an electric field across the channel 412, perpendicular to worm flow. The channel 412 comprises a plurality of micropillars 315 which function to provide confinement in the vertical direction, enabling worms that are non-responsive to the electric field to move along a straight line in the horizontal direction.

Worms were introduced at a constant small flow rate of 10-40 μl/min at the inlet 410. A constant electric field of 4-5 V/cm was applied in the vertical direction between the two separation electrodes 416 and 418. Responsive worms, thus, moved horizontally with the flow and vertically based on their electrotactic response. After a significant residence time of 4-5 min in the separation channel, the worms of similar electrotactic response were separated vertically and collected in different collection channels 414. This format allowed for continuous separation of the worms based on their electrotactic response.

4-Way Microjunction

In line with the continuous field flow fractionation-type separation sorter, electrotaxis was used to control the movement of C. elegan in a 4-way micro-junction. The device comprised 4 microchannels, a,b,c and d meeting at a junction. Each microchannel had a reservoir at the other end with an electrode inserted in it. The worms in a diluted suspension were fed into the bottom reservoir (c) of the device with a 10 μl/min flow rate moving towards the junction. Electric fields were applied desirably from a to b channels (linearly, from side a reservoir to side b reservoir), from a to d (from side to top reservoir) and a to d (from side to top reservoir). The worm arriving at the junction with the flow travels the cathodic channel, despite the fact that, at the junction, it could choose to move into the other two channels with no electric field or anodic bias.

EXAMPLE 7

Electric Trap Sorter

Figure 16:
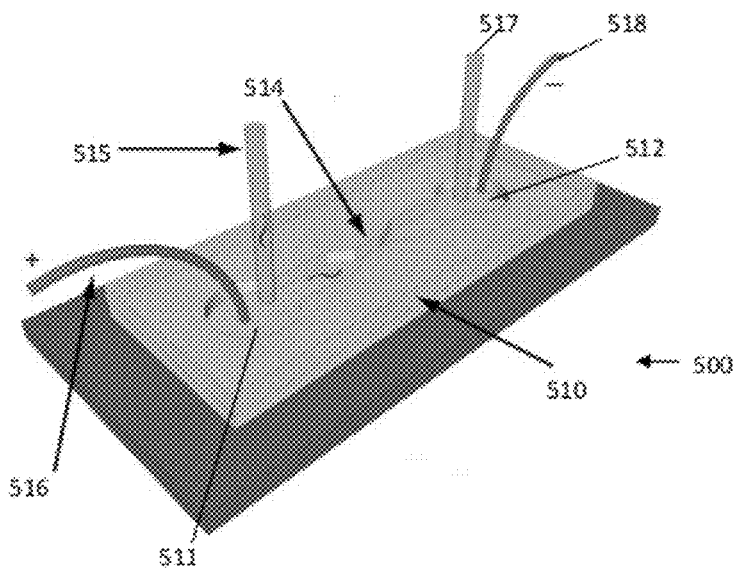
FIG. 16 shows an electric trap device for electrotactic separation.

An electric trap device 500 is also provided as shown in FIG. 16. The device 500 includes a single main PDMS microchannel 510 (e.g. 120 μm deep, 300 μm wide and 30 mm long in total) having a reservoir at both ends 511, 512 which gradually narrow to an electric trap center 514. The electric trap center 514 may be 100 μm wide and 3 mm in length. The reservoirs 511, 512 each include an electrode 516 and 518 for connection to a DC power supply and generation of an electric field across the channel 510. One of the reservoirs 511 includes an inlet 515, while the other reservoir 512 includes an outlet 517.

The electric field (EF) across a microchannel with uniform cross sectional area is EF=V/L, where V is the applied voltage and L is the length of the channel across which the voltage is being applied. Knowing that V=RI and R=ρL/A, the electric field across each microchannel section (wide-narrow-wide) in series can be calculated from equation (1):

$$EF = \frac{V}{L} = \frac{\rho I}{wt} \qquad (1)$$

where R is the electrical resistance (Ω), ρ is the electrical resistivity (Ω.m) of the media in the channel, I is the current (A), A(=wt) is the cross sectional area (m$^2$) of the channel, and w and t are the width and the thickness of the channel (m), respectively.

Equation (1) demonstrates that the ratio between electric fields of two microchannels (same thickness) arranged in series (same current passing through both) and different in width is inversely proportional to their width ratio ($EF_{narrow}/EF_{wide} = w_{wide}/w_{narrow}$).

For electrical trapping assays using the device of FIG. 16, synchronized wild type animals of various ages (n=10 each) were delivered via inlet 515 into reservoir 511 of the device. A constant electric field (16.8 V potential) was applied across the axial direction of the channel to cause electrotaxis of the worm towards the narrow electric trap 514. Three different criteria were investigated, (i) the electric field required in the wide section to initiate electrotaxis, (ii) the electric field at which the worm started to demonstrate paralysis effects (tail coil and loss of control) in the reservoir but still able to move forward towards the electric trap, and (iii) the electric field in the electric trap section which inhibited the worm from entering this section.

A range of electric fields (black column in FIG. 17b) were found to induce electrotaxis and made the worms move towards trap 514. As illustrated, this range is different for different stages of the worm, e.g. YA (2-5 V/cm), L4 (4-11 V/cm), L3 (5-15 V/cm) and L2 (7-21 V/cm). The electric field within the electric trap 514 is however always 3 fold higher than the reservoir 511. Trap electric fields which cause partial paralysis of the worm when it enters into this section also vary with the stage of the worm (gray column in FIG. 17b). However, it was observed that above the higher threshold of the gray column, worms avoid entering the trap section since they would become completely paralyzed.

Figure 17:
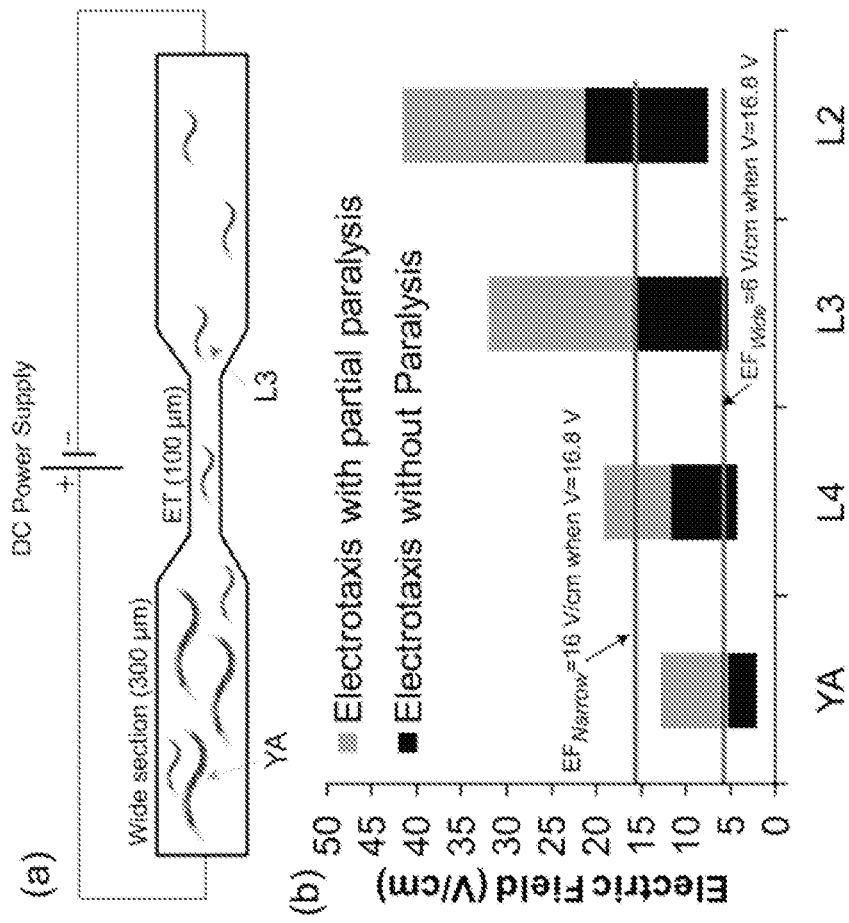
FIG. 17 shows an electric trap device (a) and electrotaxis response of *C. elegans* in the electric trap device (b)

Expecting that the worms do not like to be paralyzed and therefore will not intentionally move into the region that induces paralysis, a 16.8 V potential across the channel which contained a mixed population of L3 and YA stages was applied. The applied potential resulted in ~6 V/cm and ~18 V/cm electric fields in the wide reservoir 511 and the narrow electric trap 514, respectively. The electric field in the wide section was sufficient enough to induce electrotaxis for both L3 and YA stages (FIG. 17a). However, the electric field in the narrow section was sufficiently high to induce full paralysis for YA but not for L3 stage worms if they entered the trap 514. Thus, the YA worms did not enter the electric trap 514 but instead remained in reservoir 511, while L3 worms continued to move through trap 514 into reservoir 512. This behaviour led to automatic self sorting of the L3 worms (passed through the trap into the second reservoir) from the YA worms (did not pass through trap, but remained in first reservoir). In a 2-4 min time period, a mixed population sample of L3-YA worms, more than n=10 L3 stage worms were observed to traverse the trap in spite of the accumulation of a number of YA at the mouth of the trap.

EXAMPLE 8

Continuous Flow Sorter

Figure 18:
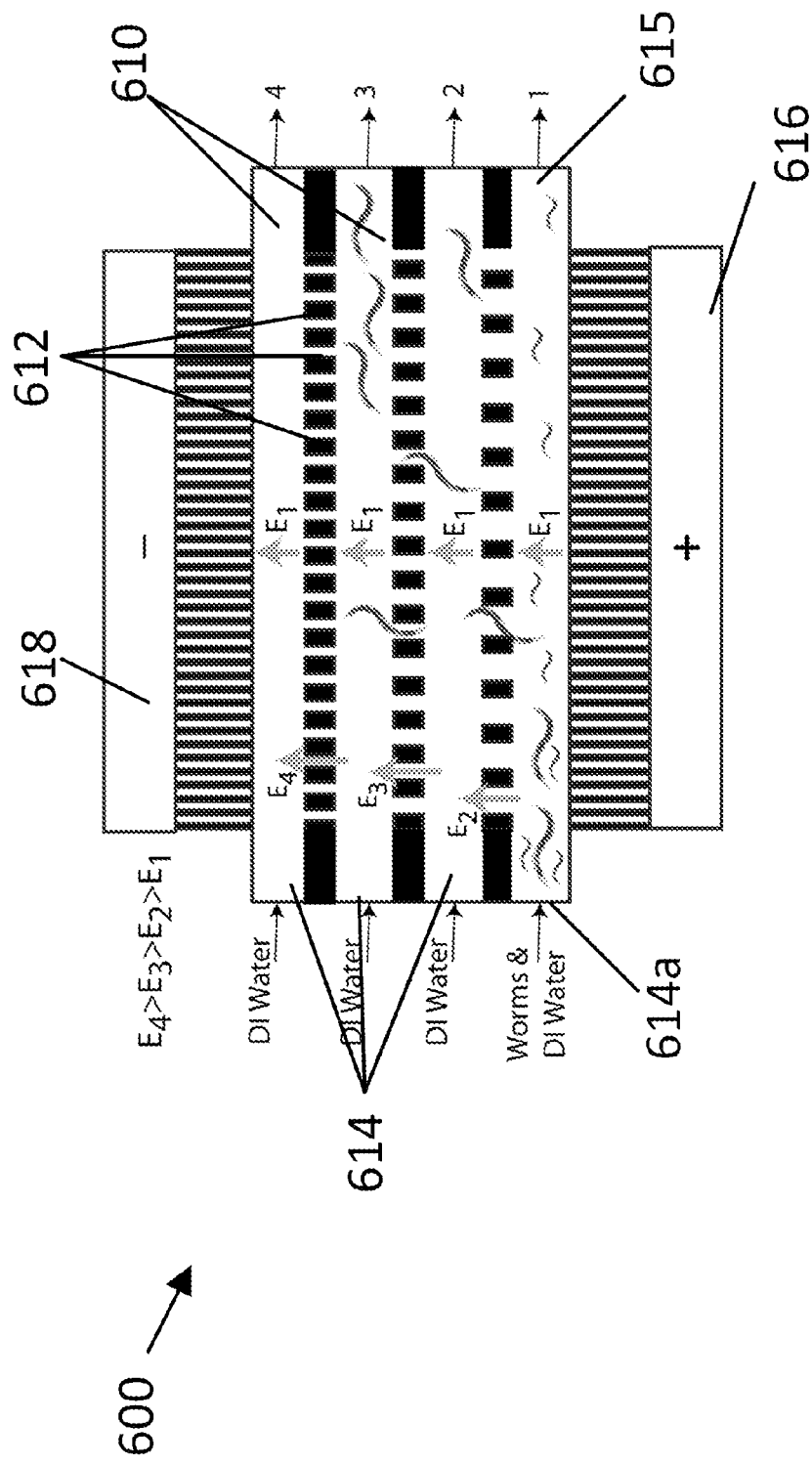
FIG. 18 shows a continuous flow worm sorter.

A continuous flow sorter device 600 as shown FIG. 18 is also provided. The device 600 comprises multiple parallel main microchannels 610 (e.g. 500 μm-wide and 80 μm high each) with an array of micropillars 612 formed between each microchannel 610. The micropillars 612 between each microchannel equidistantly spaced, but are spaced differently from microchannel 610 to microchannel 610 (the spacing between micropillars decreases from the first microchannel of the multiple to the last, e.g. micropillar gaps between first set of micropillars=100, micropillar gaps between second set of micropillars=70 and micropillar gaps between third set of micropillars=40 μm), thereby forming electric trap arrays. Inlets 614 are provided at the proximal end of each through which a flow of liquid/sample may be input via a pump into the device, and a series of collection chambers 615 exist at the distal end of each microchannel to collect sorted worms. Electrodes 616 and 618 are situated along the length of the device adjacent to the first and last microchannels of the multiple microchannels for the application of an electric field across the width of the device 600.

Electric field was applied perpendicular to the microchannels 610. Worms were introduced into the device at inlet 614a (inlet of the first microchannel of the multiple) with a continuous flow in all four microchannels using syringe pumps. When a potential is applied perpendicular to the flow (between electrodes 616 and 618), the electric field between the micropillars 612 is greater than that in the microchannel regions. Since the spacing between micropillars 612 decreases from the first microchannel 612 (1) to the last microchannel 612 (4), the electric field between micropillars also increases as shown in FIG. 18 from E1 in each microchannel, to E2 in the first set of micropillars, E3 in the second set of micropillars and E4 in the last set of micropillars. Thus, E1 was set in a range of response for the desirable worms while providing micropillar electric fields so as to exclude other stages of worm.

To quantify the performance of the device 600 in terms of separation, an efficiency parameter was defined as:

$$\eta_i [\%] = \left| \frac{G_i}{G_0} - \frac{H_i}{H_0} \right| \times 100 \quad (2)$$

where $G_0$ and $H_0$ represent the total number of adult and L3 worms fed into the device. $G_i$ and $H_i$ are the number of adult and L3 worms in output i (=1, 2, 3, or 4) in FIG. 18.

Figure 19:
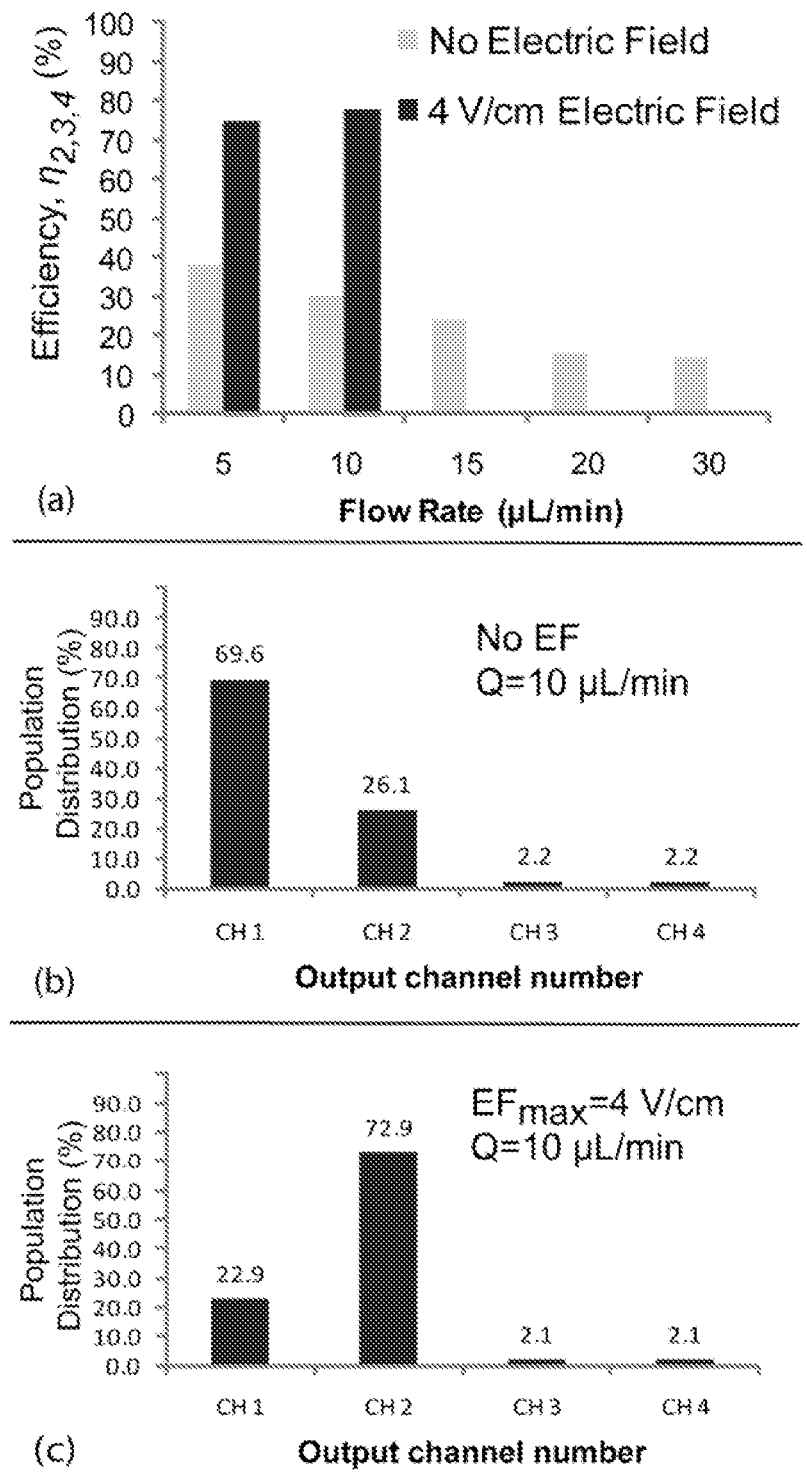
FIG. 19 shows the separation of adult worms from a mixture of adult and L3 stage worms in continuous worm sorter device at various flow rates and electric fields (a), as well as the population distribution among 4 output channels in the device with no electric field and a flow rate of 10 µL/min (b) and with an electric field of 4V/cm and 10 µL/min flow rate (c)

A mixture of adult YA ($G_0$=100) and L3 ($H_0$=100) worms were used in all experiments. Electric fields and flow rates of 2<E1(V/cm)<5 and 5<Q(μL/min)<30 were used in preliminary characterization experiments (FIG. 19a). Testing the mixture of L3 and YA with E1=4 V/cm electric field in the microchannels (leading to E2=8 V/cm, E3=11.5 V/cm, and E4=20 V/cm), L3 stages did not become separated from the input stream (H1=100 and H2=H3=H4=0) since E1 was less than the minimum response range of L3 stage. But the YA stages were able to respond to E1, pass through E2 trap (still lower than their threshold), but get trapped at E3 level (FIG. 19c).

FIG. 19a also shows the effect of different flow rates on separation efficiency for adult worms with either E1=4V/cm or no electric field. Efficiency increased from 14.5% to a maximum of 38% by decreasing the flow rate from 30 μL/min to 5 μL/min in the absence of any electric field. However, loading of the worms was difficult at lower flow rates.

Distribution of worms among the 4 outlet channels with no electric field and 10 μl/min flow rate is shown in FIG. 19b. Increasing the electric field enhanced the efficiency up to 72.9% for adult worms with an optimum flow rate and electric field of 10 μL/min and 4 V/cm (FIG. 19c). The optimum represents the balance between the electrotactic response of the adult worm and its residence time in the microchannel dictated by flow velocity. High electric field intensity in the second micropillar row (E3) prevented adult worms from passing from channel 2 to 3 in FIG. 19c. By lowering the E1 value and hence E2-4, worms can be collected from output 3 and 4 as well.

EXAMPLE 9

Semi-Continuous Sorter

Figure 20:
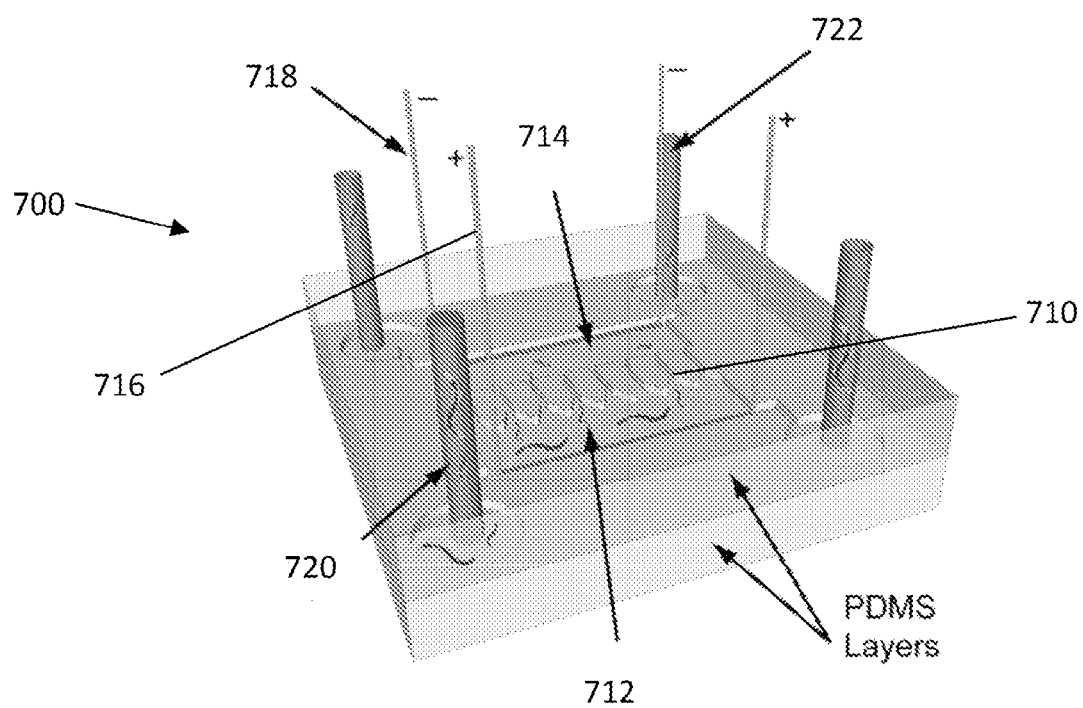
FIG. 20 shows a semi-continuous electrotactic sorter.

A semi-continuous sorting device 700 (120 µm-deep) is shown in FIG. 20. The device 700 consists of a plurality (e.g. 20) of parallel electric traps 710 as described above (e.g. 100 µm-wide, 500 µm-long, 400 µm pitch) which connect a loading chamber 712 to a separation chamber 714 (e.g. each 8 mm by 1.5 mm). Electrodes 716, 718 were situated at each of the loading and separation chambers 712, 714 in order to maintain a constant electric field throughout the device 700 across the electric traps 710. In one embodiment, 100 µm-diameter Pt wire was inserted inside the loading and separation chambers perpendicular to the axes of the electric traps 710 to produce the electric field. An inlet 720 is provided to input worms into the loading chamber 712 and an outlet 722 is provided to collect separated worms from the separation chamber 714.

Experimental

A set of experiments were conducted to study the worms' behaviour in the absence and presence of a desirable electric field in these chambers. In the first experiment, YA worms were introduced (N=10) into the loading chamber with no electric field applied across the traps. After 10 minutes, only one of the worms was observed passing through the traps into the separation chamber. This demonstrated that the worms have a preference to reside in the loading chamber in absence of any stimulating signal.

Sorting of *C. Elegans* by Developmental Stage

Figure 21:
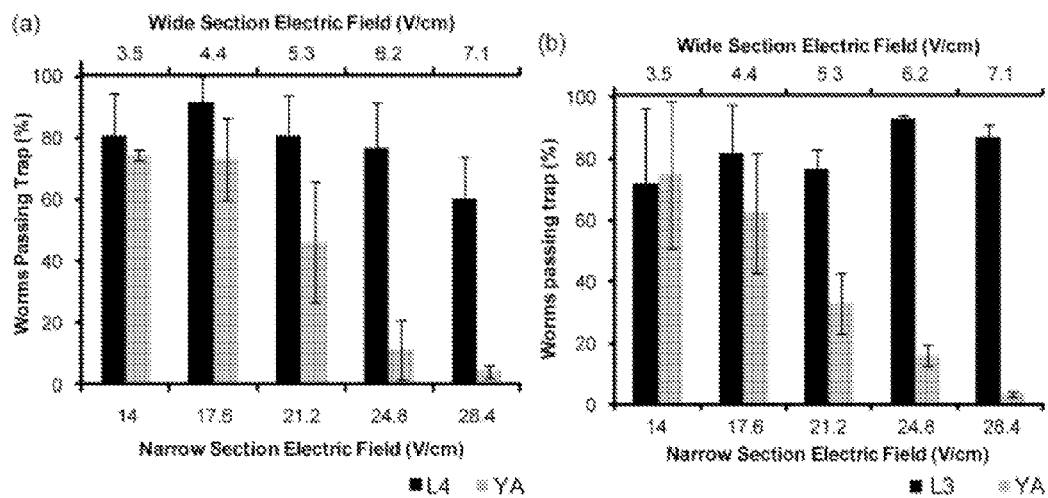
FIG. 21 shows electrotactic behaviour and sorting of YA/L4 (a) and YA/L3 (b) mixed *C. elegans* samples in semi-continuous sorter device.

Worms of two different developmental stages which were easily distinguishable by size (i.e. YA and L3 or YA and L4) were separated using this device 700. A range of electric fields (e.g. 3.5-7.1V/cm) were applied towards the separation chamber 714 to yield electric fields ranging from 14-28.4 V/cm within the electric traps 710, as shown in FIG. 21. The number of attempts that the worms made towards entering the electric traps as well as the number of successful passages through it towards the separation chamber 714 were counted for each developmental stage of *C. elegans*. The percentage of worms (out of attempted ones) passing through the trap is shown for YA/L4 and YA/L3 in FIG. 21a/b, respectively. Sorting experiments were repeated 3 times. As shown in FIG. 21, greater than 65% of the YA worms passed the electric field traps until the field in the electric trap was 14 V/cm. However, upon increasing the electric trap field strength, the percentage traversing through the trap dropped quite significantly to under 5% at 28.4 V/cm. On the other hand, this increase in electric field across the trap did not significantly affect the percentage of L3 and L4 worms passing through the electric trap and the number passing through the trap remained consistently above 60%. Between the L3 and L4 stages, the L3 worms had a higher percentage passing through the trap (~80%) at 28.4 trap electric field as compared to L4 (~60%). High trap electric field significantly inhibits YA worms (<5% pass through) followed by L4 stage worms (~60% pass through) and has virtually no effect on the L3 stage worms. L4 stage worms could be more effectively separated (80%) from YAs at 24.8 V/cm trap electric fields. It should be noted that the critical electric field needed to inhibit the worm movement for a particular stage was on an average higher than that obtained in single trap experiments (FIG. 17b) for all tested stages. This is believed to be due in most part to the shorter length (500 µm, 80% shorter) of the electric traps in the sorter device 700, resulting in less exposure time of the worm to the high strength field while attempting to pass.

Electrotactic Sorting of Neuronal or Muscle Mutants from Wildtype

Figure 22:
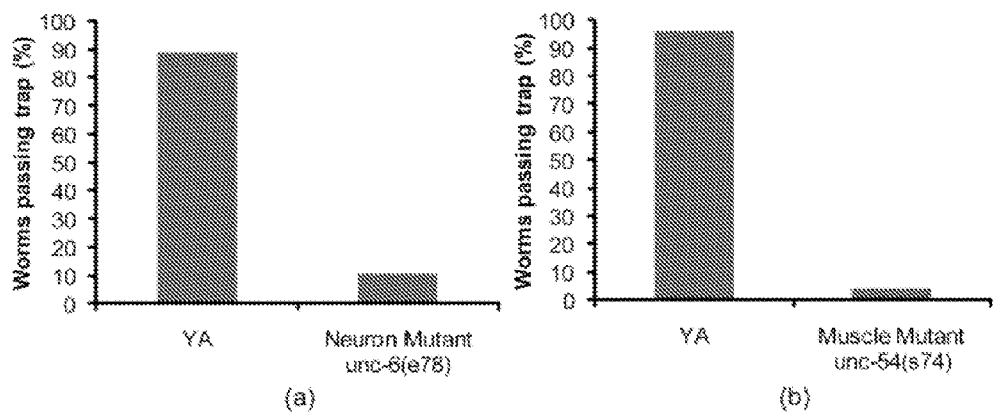
FIG. 22 shows electrotactic sorting of YA and neuronal mutant (a) and YA and muscle mutant (b) mixed *C. elegans* samples in semi-continuous sorter device.

Muscle (unc-54(s74)) or neuron (unc-6(e78)) mutant animals were mixed with YA stages in a 1:1 ratio. The wild type YA worms had GFP markers in them to distinguish them easily from the mutants. The sorting process was conducted for >50 worms at an electric field of response for adult animals (3.4 V/cm). The magnitude of the electric field in the trap was set so that the wild type YAs which respond to the electric field would be able to pass through the trap. The mutants would generally not pass through the trap due to the electric field. The worms that were able to cross the electric trap were collected from the separation chamber in a Petri dish and counted under the florescent microscope. It was found that 89% of passed worms (n=64) were wild type and only ~11% were neuron mutants (FIG. 22a). Between wildtype and muscle mutants, 96% wild type passed through the trap, while only 4% of the muscle mutants passed through the trap (n=52) (FIG. 22b).

Young and Old Adult Electrotactic Sorting

A similar approach was used to separate young from old adult worms that are similar in size. It has been reported that the electrotaxis swimming speed of worms reduces by 70% as they age (for a week) following the YA stage. In order to demonstrate this type of sorting, a mixed population of old adult (OA) (4 days) and GFP-tagged YA worms (>64 worms) was prepared in 1:1 ratio. Since both stages are highly sensitive, a low electric field (1.8 V/cm) was utilized to perform this sorting experiment.

Figure 23:
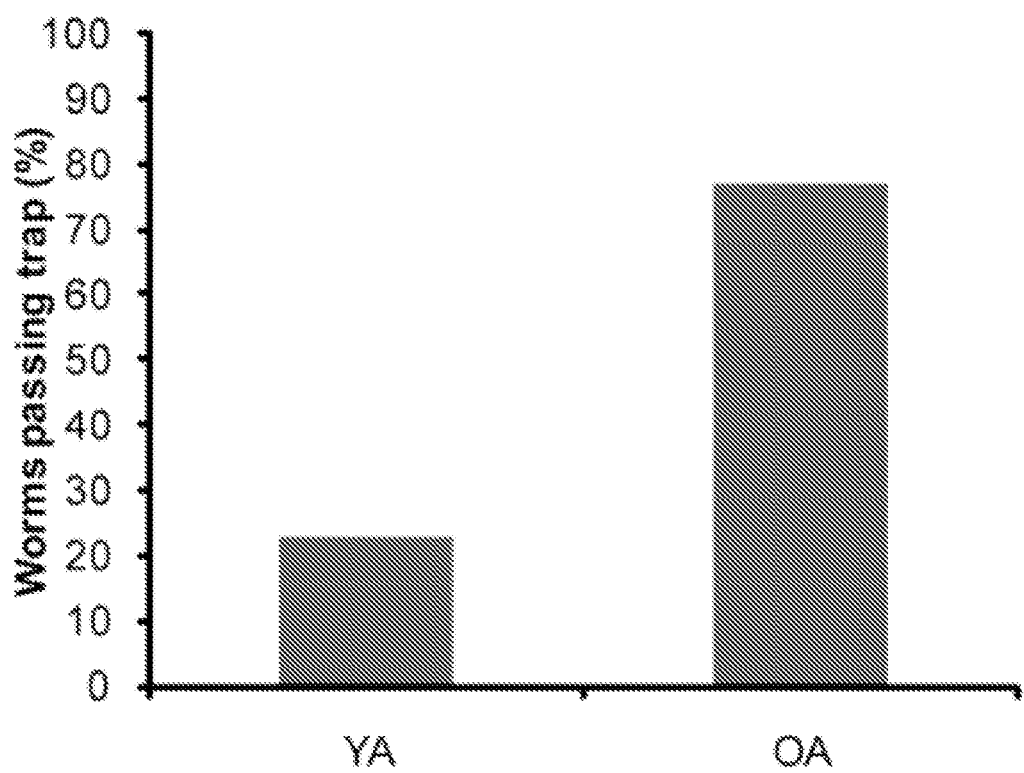
FIG. 23 shows electrotactic sorting of young and old adult *C. elegans* mixed sample in semi-continuous sorter device.

Surprisingly, it was observed that the older animals are even more sensitive to the electric field. From the sample extracted from the separation chamber, of more than 64 worms, approximately 77% were OA and 23% were YA (FIG. 23).

EXAMPLE 10

Design and Development of Microfluidic Storage Device for *C. elegans*

Figure 24:
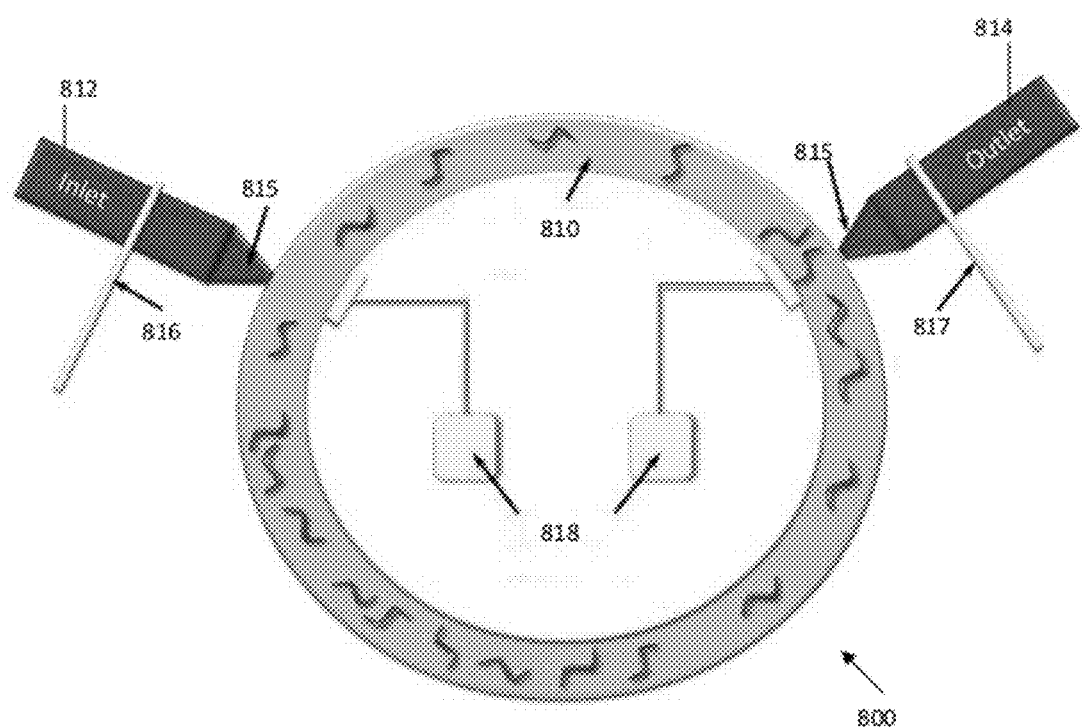
FIG. 24 shows a storage ring channel for collection of separated worm with narrow distribution of electrotactic response.

Worms are highly mobile. Even in the absence of an electric field, they continue to move in random directions. A microfluidic storage device 800, as shown in FIG. 24, is provided that stores worms and permits their continuous circulation. The device 800 comprises a ring-shaped microchannel reservoir 810 having an inlet 812 and an outlet 814 which include entropic traps 815 such that in the absence of an electric field the entropic variation between the reservoir 810 and the inlet 812/outlet 814 prevents escape of the worms. However, in the presence of electric field, there is a strong motive stimuli that attracts the worms to overcome the entropic barrier and allows them to enter or exit the device.

Iso-electrotactic worms arrive at the inlet channel 812 and are prevented from entering into the device due to the entropic trap 815. Actuation of an injection electrode 816 at the inlet 812 and the let side control electrode 818 (cathode) creates an electric field that allows the worms to be injected into the storage ring 800. The dimensions of the ring are such that the worm under random motion will prefer to reside in the larger microchannel 810 rather than enter the narrow confinement of the entropic trap 815 at the inlet 812 or outlet 814. Sufficient food (M9 solution) and oxygen can be provided by recirculating the fluid in the storage ring using macroporous membranes (1-10 micrometers pore size) that retain the worm within the device. When worms need to be arrayed, an electric field is applied across the outlet 814 with the ejection electrode 817 at the cathode and this electrical stimuli will allow the worms to overcome the entropic barrier 815 to exit the device.

Various designs of such entropic traps may be used to optimize a protocol for efficiently capturing worms based on their age/size. The entropic traps may be integrated with the microchannel storage ring and optimized for worms of various age/size. Nutrient delivery means may also be included within the entropic traps to grow worms in a physiological manner. For example, macroporous membranes (pore sizes 1-10 μm) may be integrated into a portion of the microchannel ring wall such that bacteria and oxygen can diffuse into the reservoir from an adjacent microchannel.

EXAMPLE 11

Automated Arraying of C. elegans in Microfluidic Channels

Figure 25:
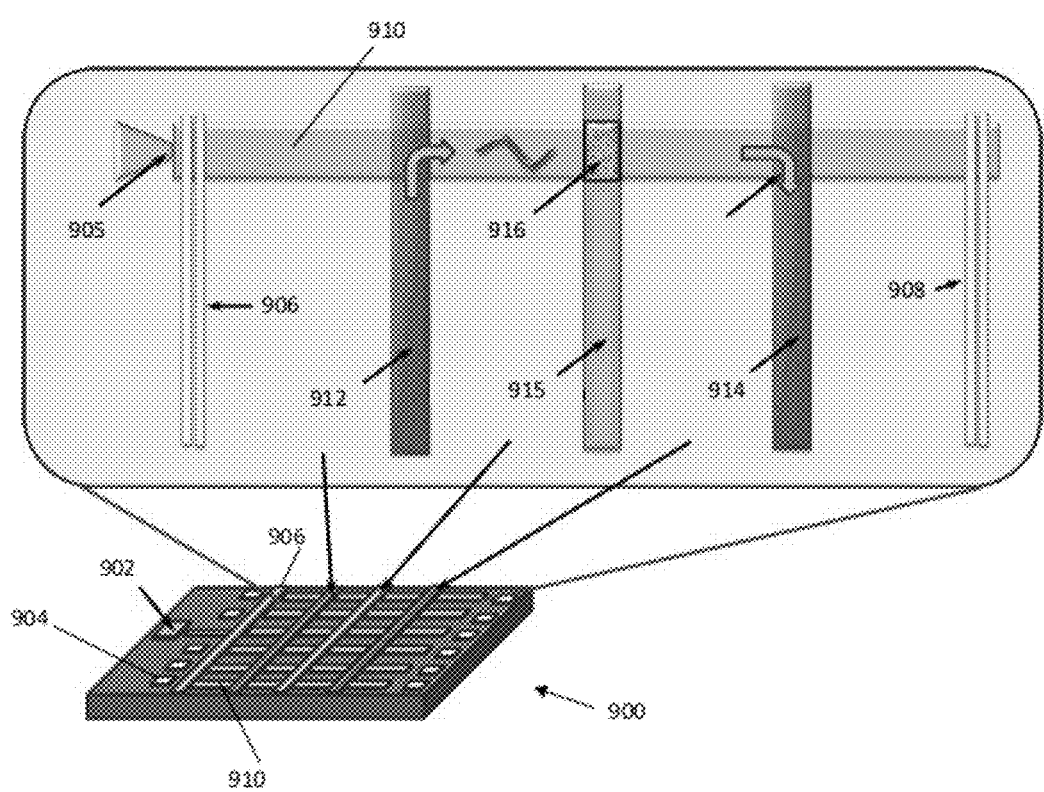
FIG. 25 illustrates a microchannel array for parallel experimentation on multiple worms.

Methods to automatically array worms into microfluidic channels where they will be exposed to chemicals and tested for electrotaxis response have been developed. To conduct such a method, a microchannel array device 900, as shown in FIG. 25, is provided. The device 900 comprises a worm storage reservoir 902 which is connected to a single worm holding unit 904 at the base of each of a plurality of parallel assay microchannels 910. Each assay channel 910 is to be populated by a single worm. The application of an electric field at an impedance-based entrance worm detector 906 simultaneously drives the motion of worms from the storage reservoir 902 to each assay channel 910 in parallel. The entrance of the worm into an individual assay channel 910 is detected electrically by the impedance based worm detector 906, and this feedback shuts off electric stimuli selectively in that channel, ensuring that only one worm is loaded into each channel. Storage rings, as described in Example 10, may be connected to individual assay channels via microfluidic connectors on the storage rings which have the same electrical resistance as the assay channel so that the electric field applied across the individual channels and hence the electric stimuli to the worms are identical. This will ensure that the worms populate the individual assay channels, simultaneously. Entropic traps 905 may be integrated at the entrance of the assay channel so that once one worm has entered and the electric field shut off, the trapped worm will not be allowed to exit. Since the arraying technique is electrical-based, an external circuit will multiplex and probe several thousands of these sensors in real-time to identify the event of a single worm entering an individual assay channel for thousands of channels in parallel.

Arrays of 100 microchannels, 1 cm in length, are typical. The array may have a common inlet for connection to the storage ring when desired to access worms of similar electrotactic response. The assay entrance valve 905 permits loading and confinement of loaded worms inside the assay channel 910. The entrance worm detector 906 provides electrical feedback to ensure that only one worm is loaded in each assay channel, e.g. via impedance or capacitance-based position detectors. As soon as one worm enters the region of detection, a feedback signal renders the detector to be anodically biased to prevent others worms from entering the channel, and the trapped worm from exiting. The fluid inlet 912 and outlet 914 channels are used to recirculate fluid (M9 solution) to maintain the physiological condition of the worm. The drug injection channel 915 comprises a nanoporous interface 916 for injection of defined quantities of drug compounds dynamically or in a pulsed fashion into the assay channel 910. The electrical drug injection method allows automated dosing of various combination and doses of drugs into a large number of microchannels simultaneously. Once the worms have been incubated with the drug, they are electrically collected at the entrance of each assay channel 910 and simultaneously made to traverse the channel 910 to determine movement characteristics. The worm detector 908 (similar to detector 906) at the end of the channel 910 detects the arrival of the worm. Worms that have been exposed to drugs that remedy their neurodegenerative behaviour will arrive at the end and these chemicals and their doses can be identified.

The worms exposed to chemicals for 3 days inside microchannels may be examined by electrotaxis. Depending upon the effect of chemicals, the speed of worms or the time of their arrival at a detector at the far end of the channel may differ from a control worm, e.g. a Htn-polyQ control worms.

In order to perform this assay, chemical compounds are dosed accurately into assay channels simultaneously and the worm is immobilized at a drug dosing region, e.g. a nanoporous interface 916 between the assay channel 910 and the drug injection channel 915, for a certain duration of time in order to obtain similar exposure profiles. Subsequently, an electric field is applied simultaneously to cause movement of the worms to the worm detector simultaneously. A microchannel based assay system with electrical control of dosing, worm localization and exposure, worm motion and detection simultaneously in all microchannels is, thus, provided.

The drug dosing region 916 comprises a nanoporous region that interfaces the assay channel to a microfluidic network above it, capable of convectively transporting various drugs or drug combinations to this location. Electrophoretic pumping can be used to transport precise and defined quantities of drugs into the assay channel in order to expose the worms to the drug. Electrophoretic pumps formed in the nanopores of the membrane can effectively be used to achieve digital dosing control of macromolecules, proteins and DNA in a reliable and repeatable manner. This proven method can be used to dynamically control the dosage of drugs into the microchambers over a period of time.

Since the worms move randomly under normal conditions, they may be confined underneath the nanoporous membrane to ensure sufficient exposure. This confinement is achieved simultaneously across all assay channels. In addition, application of an AC electric field at certain frequency ranges may be used to immobilize the worms in certain locations.

Figure 26:
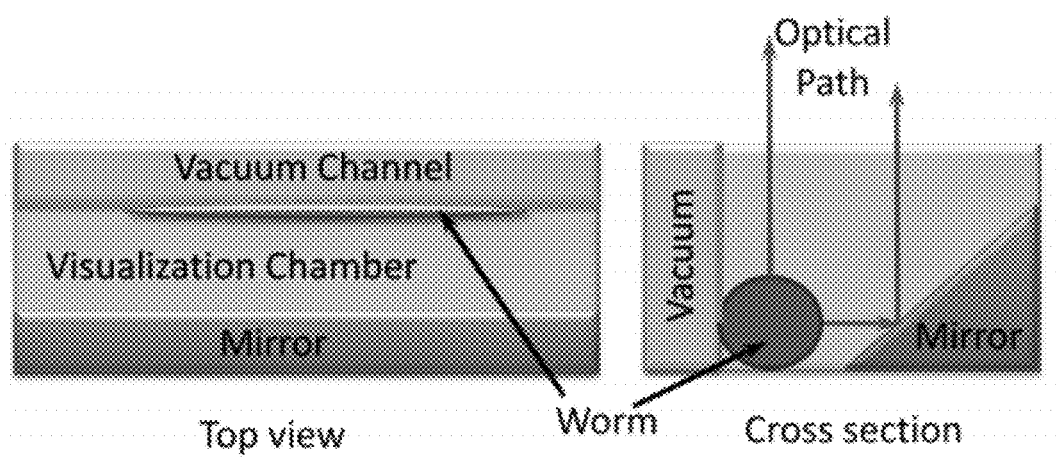
FIG. 26 shows an optical imaging chamber for worms.

After the assay, the worms may be isolated, few in number, that have been favourably or adversely affected by the screening and obtain high content information from them. Microfluidic chambers, as shown in FIG. 26, that provide optical fluorescence images at multiple angles are provided to study these selected organisms in detail.

EXAMPLE 12

Drug Screening Using Microfluidic-Based Electrotactic Screening

The toxins 6-OHDA (catalog no. 162957), Rotenone (catalog no. R8875) and Acetaminophen (catalog no. A7085) were obtained from Sigma Aldrich. MPTP (M325913) was from Toronto Research Chemicals. Desired concentrations of 6-OHDA (100 μM), MPTP (700 μM) and Rotenone (25 μM) were prepared in M9 one day before the assay and stored at −20° C. 6-OHDA solution is sensitive to light and therefore it was kept in the dark. A stock solution of Acetaminophen (10 mM) was prepared and stored at −20° C. At the time of toxin assay, the stock solution was diluted to 100 µM final concentration.

All assays with toxins were done using L1 stage worms. Synchronized L1 worms were exposed to toxin solutions for different time periods with mild shaking on a rotating platform. At the end of the time period, tubes were briefly centrifuged to remove drug solution and worm pellets were diluted with 100 µM9 buffer and were plated on normal NG agar plates.

L1 animals treated with 5 mM 6-OHDA showed extreme sluggishness, uncoordinated movement, protruding vulva, growth arrest and early larval lethality. Some of these worms were loaded into the channel of a device as shown in FIG. 1 and found that they were practically immobile and unresponsive to the electric field stimulus. Reducing 6-OHDA exposure (100 µM for 4 hr) enabled a successful electrotaxis assay. Worms exposed to 100 µM 6-OHDA for as little as 30 min showed abnormal electrotactic response demonstrating sensitivity of the assay. The MPTP and Rotenone treatment protocols were also modified. For MPTP, exposure of L1 worms to 1.4 mM toxin for 3 days resulted in worms that were almost completely uncoordinated and paralyzed and thus not suitable for electrotaxis assay. A range of conditions were tested and it was found that worms exposed to 700 µM MPTP for up to 8 hrs showed obvious defects in the channel assay. Interestingly these animals appeared fairly active and healthy on NG agar plates, once again demonstrating that the present electrotactic assay is sensitive in detecting behavioral abnormalities. Finally, for rotenone a micromolar range of concentrations was tested and it was found that worms exposed to 25 µM of drug for less than 12 hrs showed morphological defects similar to MPTP in repeated trials. It wad determined that animals treated with 25 µM of Rotenone for 1-8 hr appeared largely healthy on the plate but had abnormal electrotactic movement.

Electrotaxis Assay and Data Analysis

Experimental design was as described Rezai et al., ibid. Electric field was fixed at 3V/cm. Each worm was allowed to move a minimum distance of 5000 µm inside the channel, of the device as shown in FIG. 1, in one direction. Then, the direction of the electric field was changed and the worm was allowed to move the same distance in the opposite direction. The movement of each worm was recorded using a Nikon Coolpix P5100, NY, USA. The captured videos were analyzed using the ImageJ NIH image module. Three parameters—U-turn, head movement and speed—were used to characterize the behaviour of animals. For U-turn, the time (in seconds) that was taken by a moving worm to come to a stop and turn to the opposite direction after the electric field direction was reversed was recorded. Most wild type worms (~90%, see results) were able to change direction in less than 10 seconds. Worms taking 10 sec or longer were considered to have an abnormal response. For the head movement analysis, the number of full sine waves (i.e., spanning up to three-fourth of the channel width) that a worm makes within a 30 sec. duration were determined. Wild-type worms make full sine waves in majority of cases with failures typically being less than 25%. Therefore, a threshold of 25% to place a worm in normal or abnormal category was used. In the present assay, 90% or more wild type worms were observed to be below the threshold (see results). To analyze speed, the time taken by a worm to move a distance of 5000 µm in a given direction was used. Speed was measured in both directions of movement and the average value was used as a true response. Wild type animals typically moved with a speed of 215 µm/sec and above. Therefore, animals moving slower than 215 µm/sec were considered to have an abnormal response.

Results

Since wild type worms move towards the cathode when exposed to a low voltage DC electric field inside the microfluidic channel. This response, termed "electrotaxis", requires intact neuronal and muscular systems. Therefore, the role of these neurons in the microfluidic channel assay was tested.

In addition to testing genetic mutants with abnormal neuronal function, namely unc-6, osm-5, tax-6, cat-2, dop-1, dop-2, dop-3), the response of worms exposed to a very low concentration (10 µM) of levamisole (an anthelmintic drug that acts as acetylecholine agonist in body-wall muscle) was tested. The tested worms had reduced movement (only 5 worms were tested). Thus, the assay system can reveal abnormalities in neuronal as well as muscular activities using movement as a read-out.

Electrotactic Response of Worms Exposed to Neurotoxins

Having established that the assay system detects movement defects in worms with altered neuronal activity, the response of animals treated with certain toxins that cause degeneration of sensory neurons, namely, 6-OHDA (6-hydroxydopamine, a hydroxylated form of dopamine), MPTP (1-methyl 4-phenyl 1,2,3,6-tetrahydropyridine) and Rotenone (an organic pesticide), all of which have been shown to cause preferential degeneration of dopaminergic neurons in a specific region of brain (substantia nigra) in vertebrates, was tested. These toxins also cause degeneration of DA neurons in *C. elegans*. Three parameters (U-turn, head movement and speed as described above) were used to characterize these defects in detail.

Figure 27:
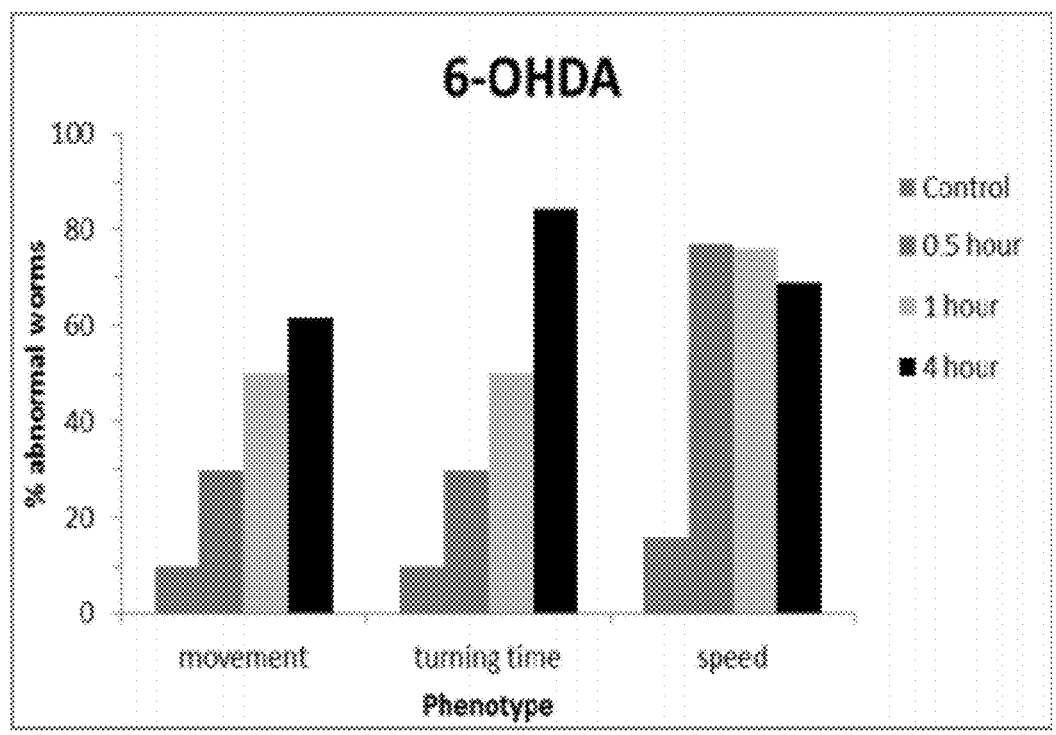
FIG. 27 graphically illustrates movement behavior of worms treated with 6-OHDA using an electrotaxis assay.
Figure 28:
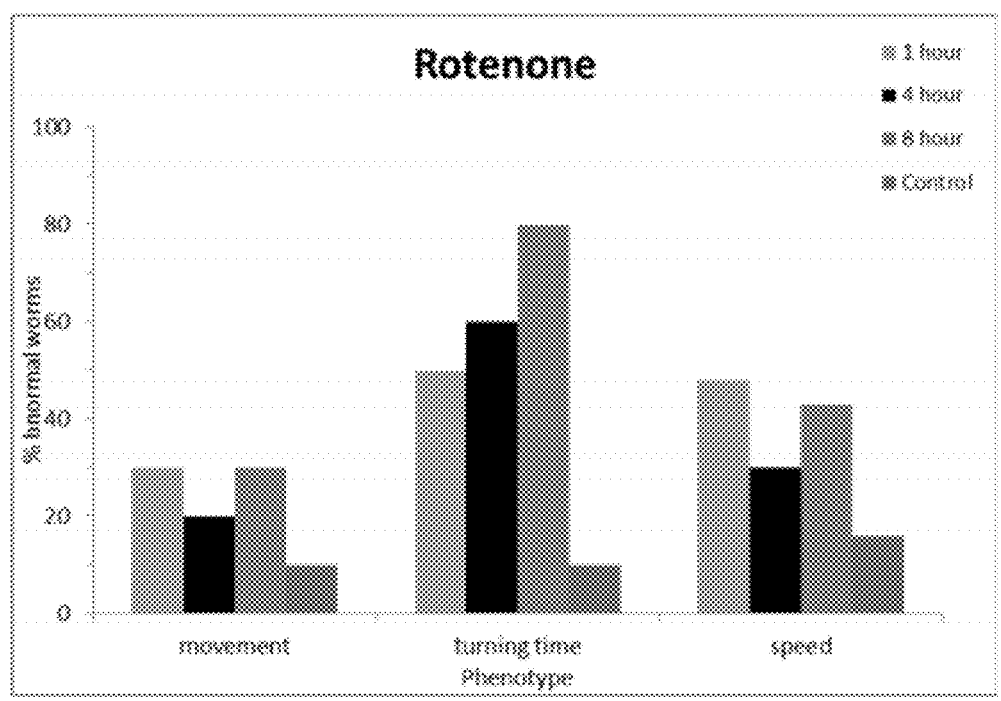
FIG. 28 shows electrotactic analysis of movement behavior of worms exposed to Rotenone.

In the present assay, 6-OHDA exposure was found to cause U-turn defect in 30-80% of worms within 4 hour exposure (FIG. 27). The penetrance was similar in MPTP-treated worms with defect in 30%-70% of worms. U-turn response was most sensitive to Rotenone treatment; with a gradual increase in the proportion of defective worms (50% to 80%) within 1-8 hr exposure time (FIG. 28).

Figure 29:
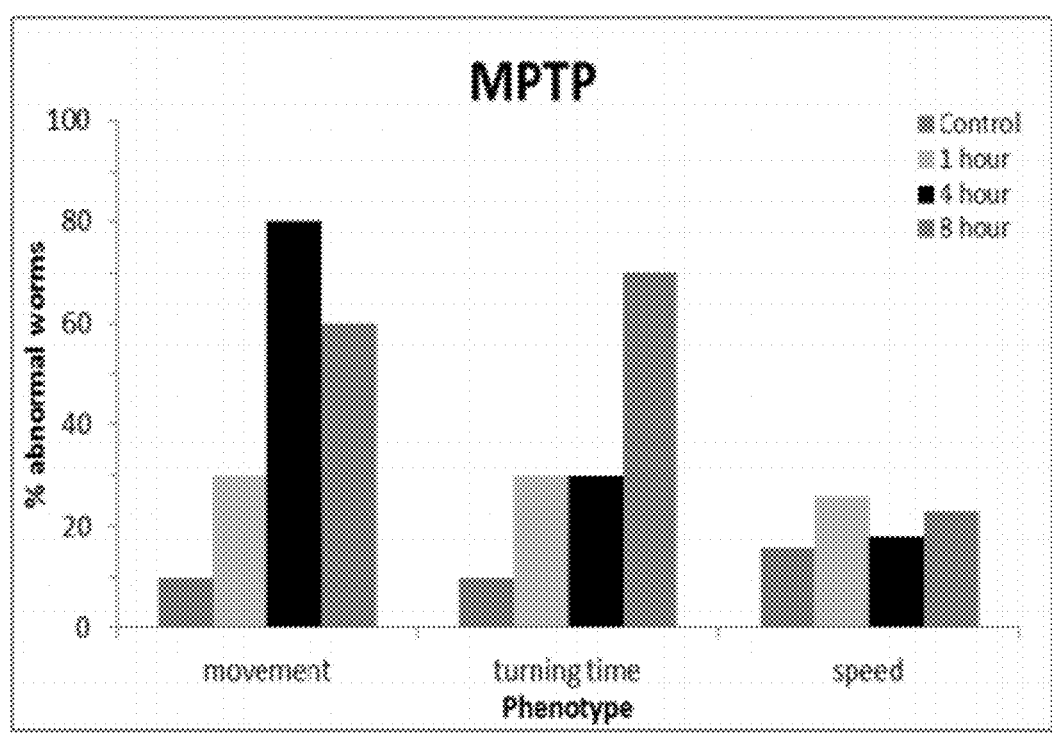
FIG. 29 shows electrotactic analysis of movement behavior of worms exposed to MPTP.

Similar to the U-turn, head movement was also highly defective in toxin-treated animals. In the case of 6-OHDA, about one-third of worms exhibited a defective response following 30 minutes toxin exposure. The proportion of defective animals gradually went up (to 50%) as the exposure time was increased to 1 hr (FIG. 27). By 4 hour exposure 61% of the worms were defective. Rotenone treatment caused a less severe head movement defect. Thus, only up to 30% worms showed abnormal head movement response even after 8 hrs of toxin exposure (FIG. 28). In comparison to 6-OHDA and Rotenone, MPTP exposure had a severe defect in head movement response. A 4 hr MPTP exposure caused defects in 80% worms (FIG. 29). A longer toxin exposure did not make it worse suggesting that this duration was enough to cause maximum defect in movement in response to electric field stimulus.

Movement speed of toxin-treated animals was also tested. Treatment with 6-OHDA resulted in most defective response compared to the other 2 toxins (FIG. 27). On the other hand, MPTP showed a wild type response in all 3 conditions tested (FIG. 29). Finally, Rotenone exposure caused 48% defect in the speed of animals (FIG. 28).

Morphological and Behavioral Analyses of Neurotoxin-Treated Animals

Worms exposed to high doses and long exposure of 6-OHDA, MPTP and Rotenone exhibit uncoordinated movement, abnormal morphology, reduced size, and retarded or arrested growth. These phenotypes are in agreement with published studies. As described in the methods section lowering the concentration and exposure time of toxins resulted in significant reduction in the proportion of animals showing morphological and behavioral abnormalities.

Figure 30:
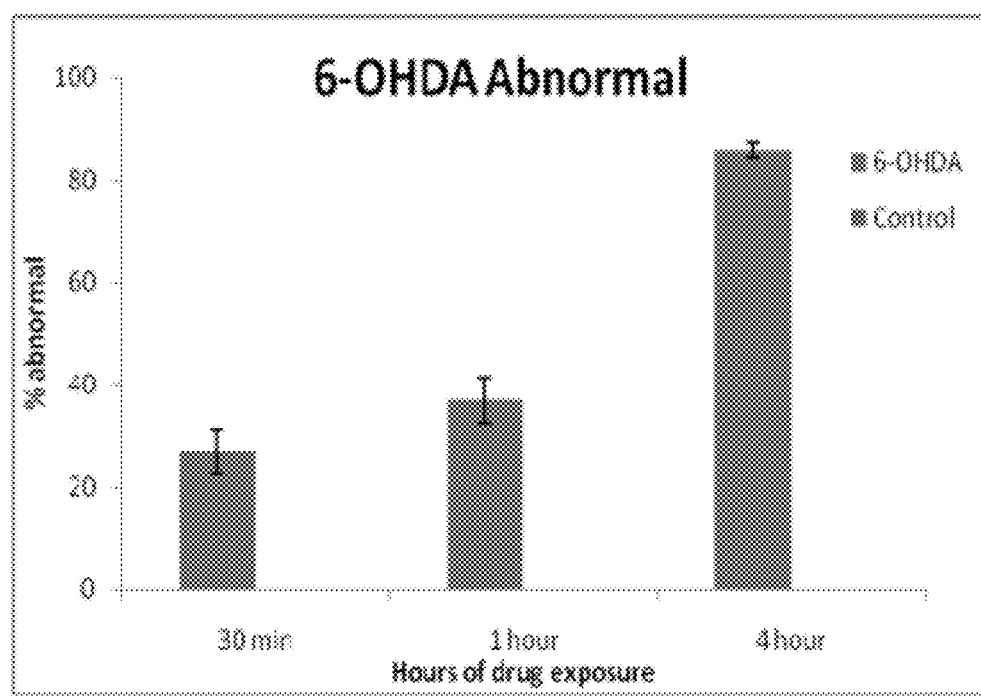
FIG. 30 shows plate level analysis of 6-OHDA exposed worms.
Figure 31:
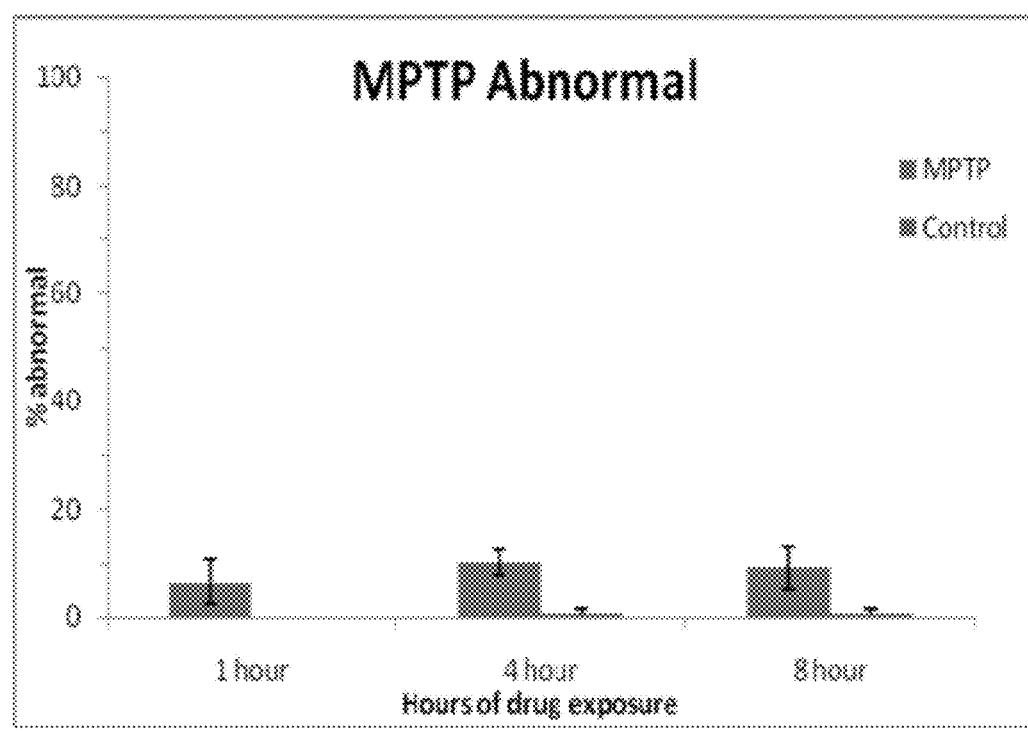
FIG. 31 shows plate level analysis of MPTP exposed worms.
Figure 32:
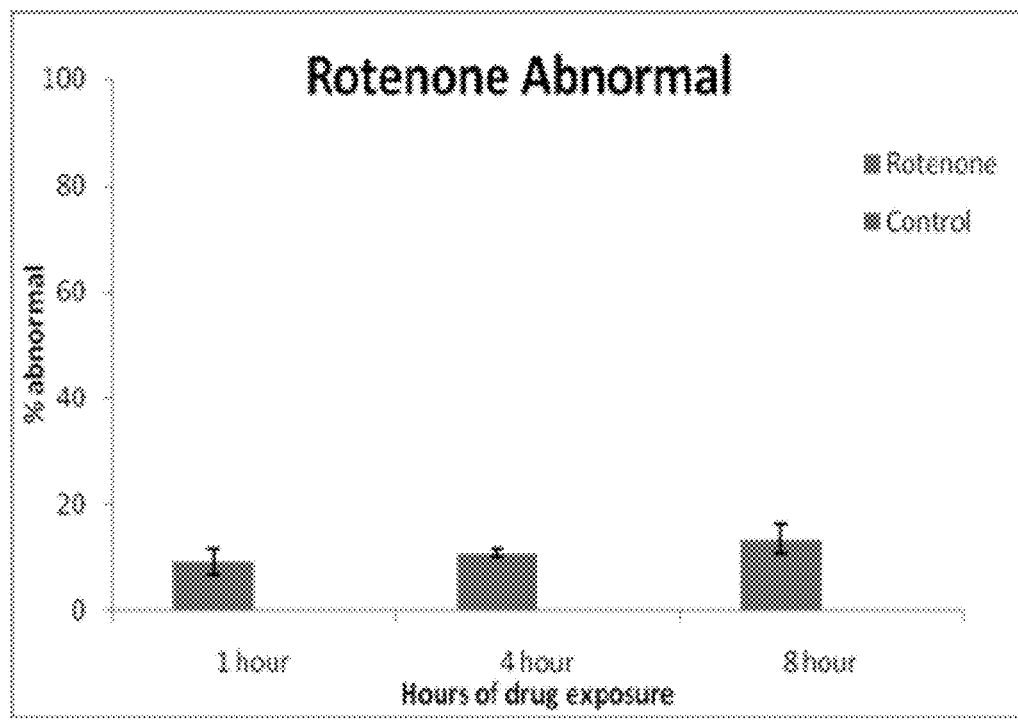
FIG. 32 shows plate level analysis of Rotenone exposed worms.

Among the three toxins, 6-OHDA had the highest impact. A 4 hr exposure resulted in uncoordinated phenotype in most of the animals (86%). Occasionally animals also showed morphological defects such as protruding vulva (Pvl). Reducing the exposure time to just 30 min resulted in fewer worms (one-quarter) showing a weak uncoordinated phenotype (FIG. 30). Unlike 6-OHDA, exposure to MPTP and Rotenone had only subtle and low penetrant movement defects (FIGS. 31 and 32). This was revealed by slow reaction of animals when touched on the head or tail. In no case was a reduced size and growth arrest phenotype observed, and except for the 4 hr 6-OHDA condition, all other animals appeared fairly healthy, active and fertile.

Exposure of Neurotoxins Causes Degeneration of Dopaminergic Neurons

Previous work has demonstrated that dopaminergic neurons are highly sensitive to all three toxins noted above. Administration of 6-OHDA in a mammalian model produces various biological effect including increase level in reactive oxygen species (ROS) that leads to depletion of DA neurons. In the case of MPTP, it is metabolized into MPP+ which is the active toxic product that gets inside the DA neuron through the dopamine transporter. Inside the DA neuron, MPP+ has multiple targets including the inhibition of mitochondrial respiratory enzyme complex I that leads to increase level of ROS. Exposure to rotenone in rat and *Drosophila melanogaster* model has shown to cause apoptosis; oxidative damage, and degeneration of dopamine neurons. Damage of dendritic process of DA neurons has been shown upon exposure to 6-OHDA. MPTP also cause depletion of DA neurons as the florescence in the neuron specific marker loss after treatment. Rotenone causes decrease in survival rate.

Figure 33:
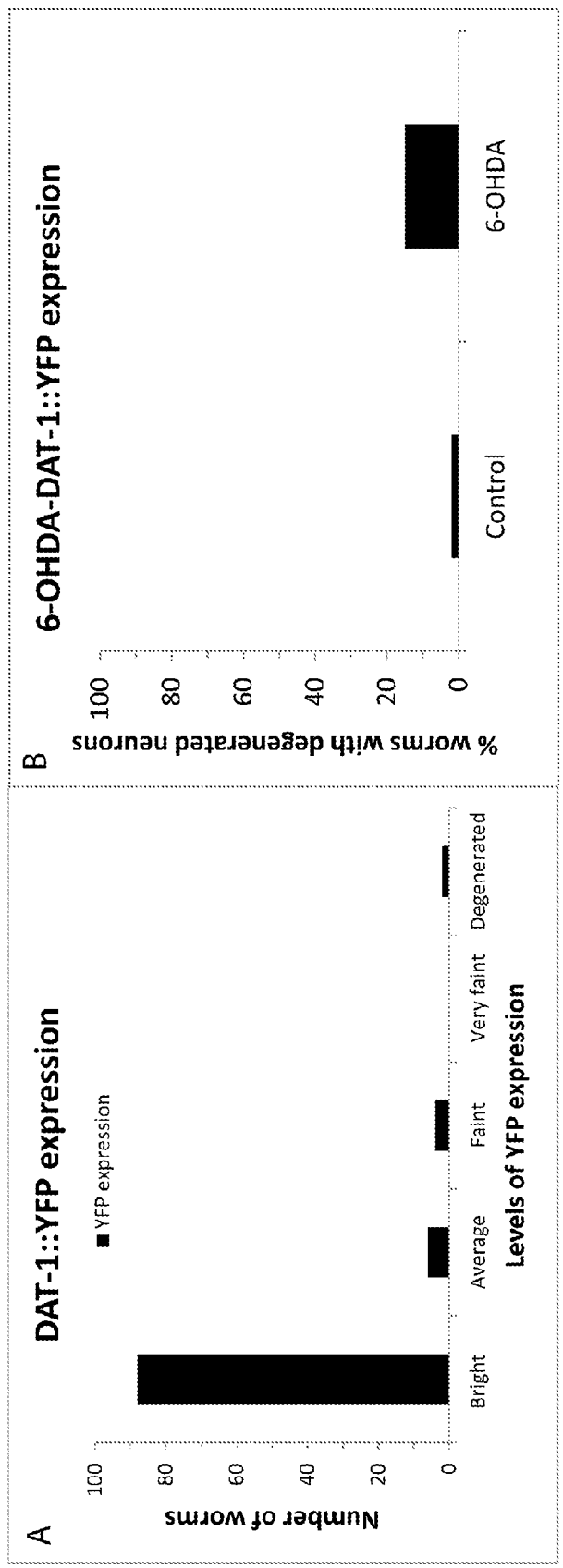
FIG. 33 graphically illustrates YFP expression in a transgenic animal that expresses the DA transporter (a) and YFP expression following toxin-induced degeneration of DA neurons (b)

To visualize the toxin-induced degeneration of DA neurons in the present assay, dat-1p::yfp transgenic animals were generated (as described in Nass et al. 2002, PNAS, vol. 99(5), 3264-3269. dat-1 encodes the DA transporter and is expressed in all DA neurons. The analysis of dat-1p::yfp expression in bhEx120 animals revealed bright YFP fluorescence in CEP neurons (FIG. 33a). Exposure to 6-OHDA (100 μM) for 4 hours did not cause an obvious degeneration of DA neurons, however a longer exposure (~71 hrs) resulted in defects in 15% of animals. In these cases the dendritic processes of CEPs showed variable degeneration such that YFP fluorescence had a spotted and blebbing appearance. In some cases, the entire dendritic processes were missing.

Channel-Based Drug-Screening Assay

In order to establish a baseline to screen for neuroprotective compounds in a channel-based assay, the neuroprotective effect of acetaminophen (a known analgesic) against neurodegeneration caused by toxins as tested. Previous studies in rats and *C. elegans* had demonstrated the protection conferred by acetaminophen against MPP+, 6-OHDA and glutamate toxicity in dopamine neurons.

Figure 34:
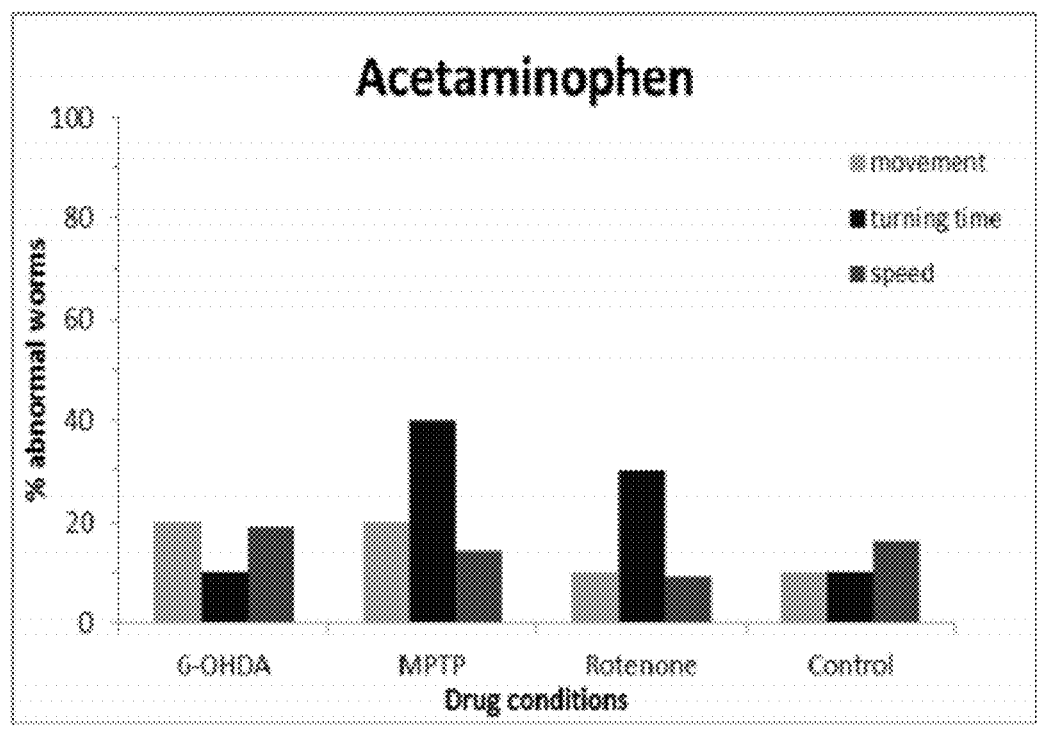
FIG. 34 shows analysis of movement behavior of Acetaminophen pre-exposed worms against 6-OHDA, MPTP and Roteneone using electrotaxis assay.

Pre-treatment of worms with acetaminophen (100 uM, 24 hrs exposure during L1 stage) prior to treatment with 6-0H DA as above, conferred a significant protection on the worms as evidenced by the electrotactic response of worms using all 3 movement parameters described above. The protection ranged from 30% to 50% (FIG. 34). In the case of MPTP, acetaminophen pre-treatment had a similar effect. The defect in head movement was decreased by 40% and U-turn by 30%. The impact of Acetaminophen on Rotenone-induced neuronal toxicity and provide first evidence that Acetaminophen protects DA neurons from the toxic effects of Rotenone. While the head movement defect was decreased by 20%, abnormalities in U-turn response and speed were lower by 50% and 38%, respectively.

In summary, the present microfluidics-based electrotaxis assay was effective to show that Acetaminophen effectively protects DA neurons against neurotoxins, and that the microfluidics-based assay is an effective drug screening tool for use to identify other protective compounds.

What is claimed is:

1. A method of stimulating nematode responses in a microfluidic environment comprising;
    exposing a mixed population of nematodes having different developmental characteristics to an electric field that stimulates different responses based on the different developmental characteristics and determining the nematode responses.

2. The method of claim 1, wherein the electric field is DC, AC, pulsed DC or a combination thereof.

3. The method of claim 1, wherein the electric field is in the range of 1-12 V/cm.

4. The method of claim 1, wherein the different developmental characteristic is selected from a group consisting of age and size.

5. The method of claim 1, wherein the response of nematode larvae differs from the response of adult nematodes.

6. The method of claim 4, wherein the nematode response increased with the age of the nematode.

7. The method of claim 6, wherein the electric field is in the range of 2-4 V/cm.

8. The method of claim 6, wherein the response of adult nematodes is greater than the response of L4 larvae and the response of L4 larvae is greater than the response of L3 larvae.

9. The method of claim 1, wherein the response is selected from a group consisting of movement, speed, direction, paralysis, turning time, extent of head movement, sinusoidal motion path, pauses and reversals.

10. The method of claim 4, wherein the nematode response increases as the size of the nematode decreases.

* * * * *